United States Patent
Huang

(10) Patent No.: US 9,132,450 B2
(45) Date of Patent: Sep. 15, 2015

(54) ELECTROSTATIC COMB DRIVER ACTUATOR/TRANSDUCER AND FABRICATION OF THE SAME

(75) Inventor: Yongli Huang, San Jose, CA (US)

(73) Assignee: Kolo Technologies, Inc., San Jose, CA (US)

(*) Notice: Subject to any disclaimer, the term of this patent is extended or adjusted under 35 U.S.C. 154(b) by 1173 days.

(21) Appl. No.: 12/296,090

(22) PCT Filed: Apr. 4, 2007

(86) PCT No.: PCT/US2007/065932
§ 371 (c)(1),
(2), (4) Date: Oct. 3, 2008

(87) PCT Pub. No.: WO2007/115294
PCT Pub. Date: Oct. 11, 2007

(65) Prior Publication Data
US 2009/0152980 A1    Jun. 18, 2009

Related U.S. Application Data

(60) Provisional application No. 60/744,242, filed on Apr. 4, 2006.

(51) Int. Cl.
*H02N 1/00* (2006.01)
*H01L 21/00* (2006.01)
(Continued)

(52) U.S. Cl.
CPC ............. *B06B 1/0292* (2013.01); *B06B 1/0238* (2013.01); *G01N 29/2406* (2013.01); *Y10T 29/49005* (2015.01)

(58) Field of Classification Search
CPC . B06B 1/0238; B06B 1/0292; G01N 29/2406
USPC ........ 310/309; 600/459; 73/514.32; 367/174, 367/181
See application file for complete search history.

(56) References Cited

U.S. PATENT DOCUMENTS 1,839,130 A * 12/1931 Thomas .................. 381/191
4,677,336 A    6/1987 Kushida et al.
(Continued)

FOREIGN PATENT DOCUMENTS

GB    2076970    *    5/1981    .............. B22D 17/00

OTHER PUBLICATIONS

J Mohr, M Kohl, W Menz; Micro optical switching by electrostatic linear actuators with large displacements; Proc. 7th Int. Conf. Solid-State Sensors and Actuators (Transducers '93), Yokohama, Japan (Jun. 7-10, 1993), pp. 120-124.*

(Continued)

*Primary Examiner* — Terrance Kenerly
(74) *Attorney, Agent, or Firm* — Lee & Hayes, PLLC

(57) ABSTRACT

An electrostatic actuator/transducer has a comb driver and can be adapted for a variety of applications, particularly as a capacitive micromachined ultrasonic transducer. The comb driver has two electrodes each connected to a set of comb fingers. The two sets of comb fingers interdigitate with each other, and in one embodiment each has a saw-toothed shape. One electrode is connected to a spring structure and movable along a vertical direction to engage and disengage the two sets of comb fingers. The movable portion is adapted to perform an actuation function and/or a sense of function. Fabrication methods for making the electrostatic actuator/transducer are also disclosed.

19 Claims, 14 Drawing Sheets

(51) Int. Cl.
*B06B 1/02* (2006.01)
*G01N 29/24* (2006.01)

(56) References Cited

U.S. PATENT DOCUMENTS

| | | | | |
|---|---|---|---|---|
| 5,375,033 | A * | 12/1994 | MacDonald | 361/281 |
| 5,780,948 | A * | 7/1998 | Lee et al. | 310/81 |
| 6,035,714 | A * | 3/2000 | Yazdi et al. | 73/514.32 |
| 6,278,169 | B1 * | 8/2001 | Sayuk et al. | 257/435 |
| 6,307,298 | B1 * | 10/2001 | O'Brien | 310/309 |
| 6,384,952 | B1 * | 5/2002 | Clark et al. | 359/224.1 |
| 6,424,504 | B1 * | 7/2002 | Abe et al. | 360/294.4 |
| 6,543,285 | B2 * | 4/2003 | Hashimoto | 73/504.14 |
| 6,705,166 | B2 * | 3/2004 | Leonardson | 73/514.32 |
| 6,815,865 | B2 * | 11/2004 | Marxer | 310/309 |
| 6,865,140 | B2 * | 3/2005 | Thomenius et al. | 367/155 |
| 6,958,255 | B2 | 10/2005 | Khuri-Yakub et al. | |
| 7,564,172 | B1 * | 7/2009 | Huang | 310/328 |
| 8,120,229 | B2 * | 2/2012 | Huang | 310/309 |
| 2002/0121145 | A1 * | 9/2002 | DeConde et al. | 73/862.046 |
| 2003/0183008 | A1 * | 10/2003 | Bang et al. | 73/514.01 |
| 2004/0212457 | A1 * | 10/2004 | Eden et al. | 333/185 |
| 2004/0267134 | A1 * | 12/2004 | Hossack et al. | 600/459 |
| 2005/0075572 | A1 * | 4/2005 | Mills et al. | 600/459 |
| 2006/0168788 | A1 * | 8/2006 | Tilmans et al. | 29/25.35 |
| 2006/0197804 | A1 * | 9/2006 | Lim et al. | 347/55 |
| 2008/0190204 | A1 * | 8/2008 | Danel et al. | 73/514.32 |
| 2009/0152980 | A1 * | 6/2009 | Huang | 310/309 |
| 2010/0242603 | A1 * | 9/2010 | Miller et al. | 73/514.32 |

OTHER PUBLICATIONS

Rosengren et al.; "Micromachined sensor structures with linear capacitive response", Sensors and Actuators A., 31 (1992) pp. 200-205.*

Rosa et al, "Enhanced electrostatic force generation capability of angled comb finger design used in electrostatic comb drive actuators", Electronics Letters, Sep. 3, 1988, vol. 34, No. 18, pp. 1787-1788.*

Ye et al., "Optimal Shape Design of an Electrostatic Comb Drive in Microelectromechanical systems", Journal of Microelectromechanical systems, vol. 7, No. 1, Mar. 1988.*

* cited by examiner

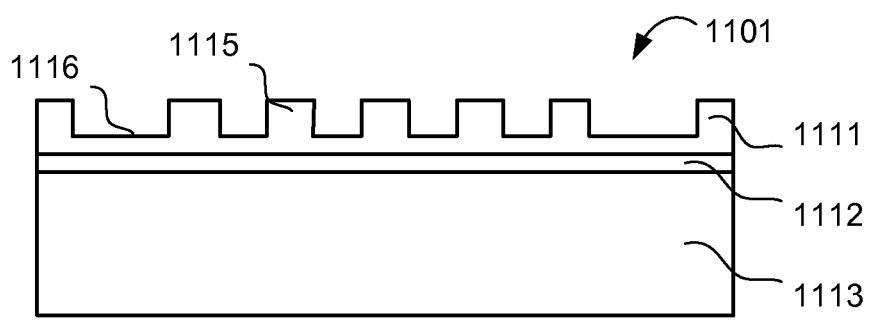
FIG. 11.1
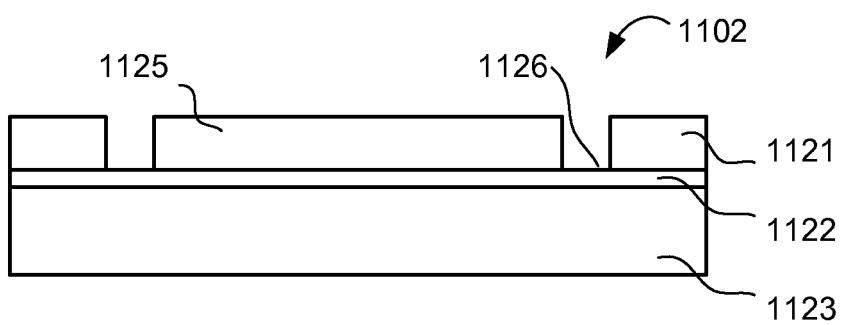
FIG. 11.2
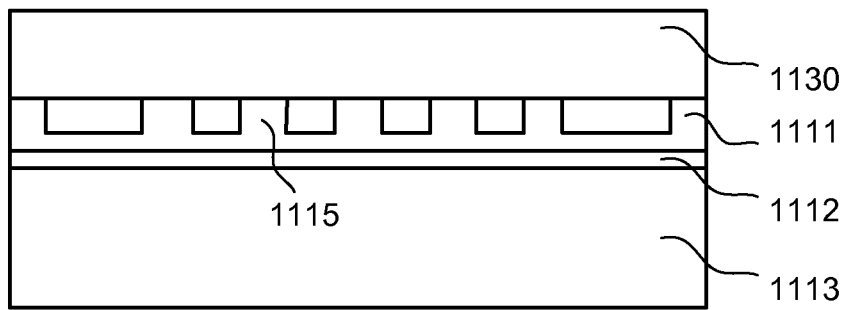
FIG. 11.3
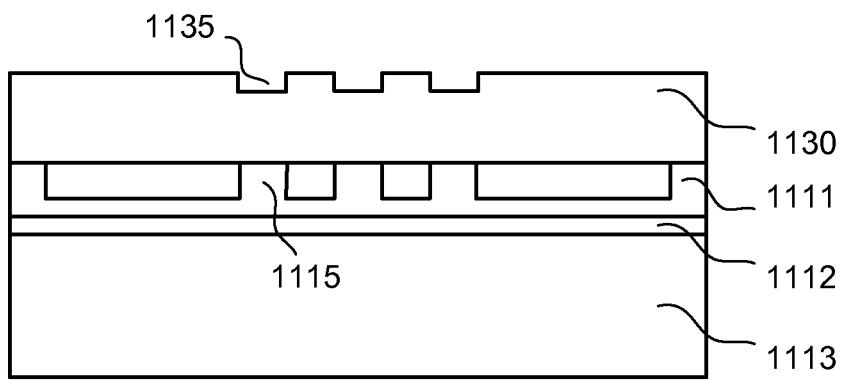
FIG. 11.4

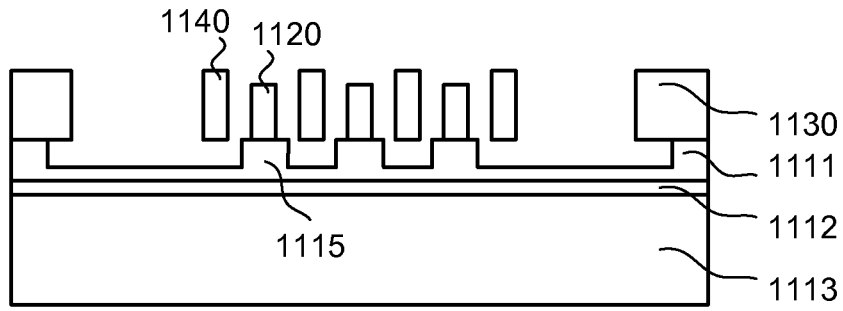
FIG. 11.5
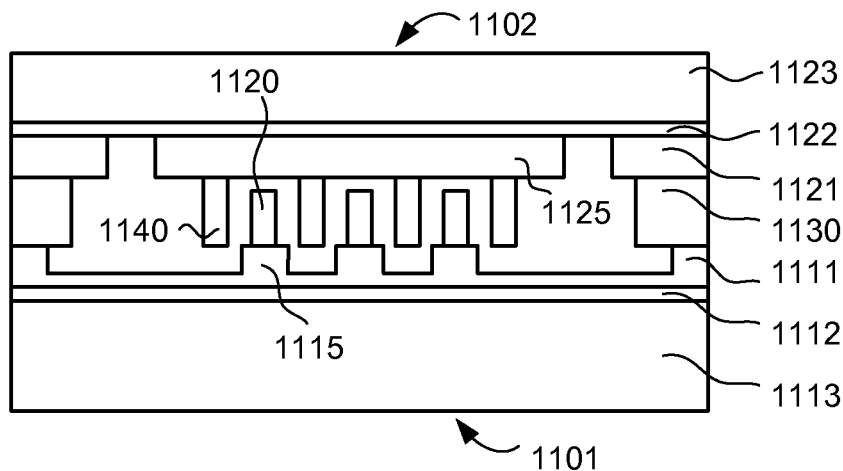
FIG. 11.6
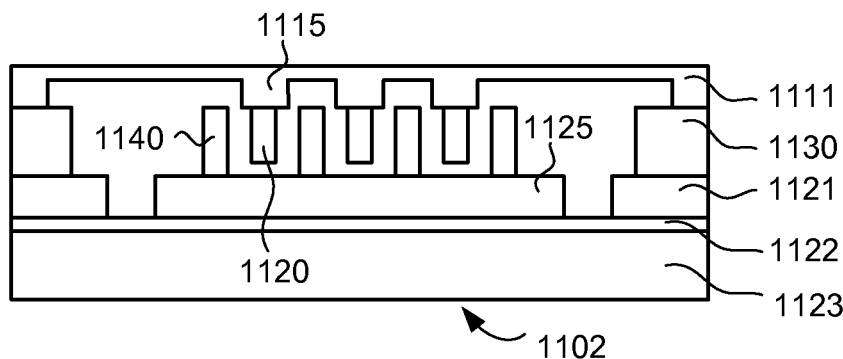
FIG. 11.7
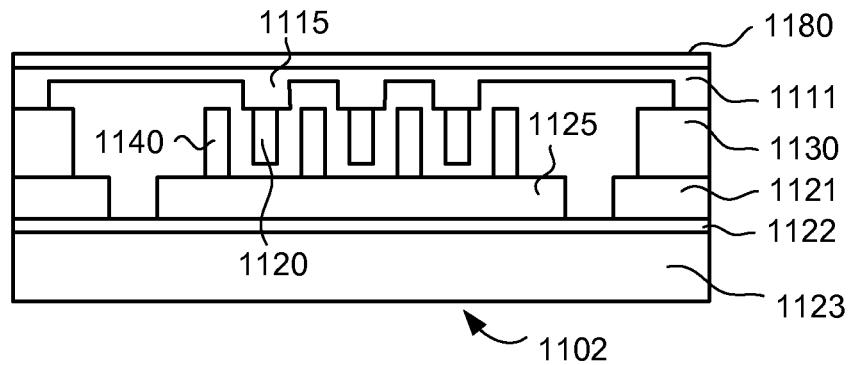
FIG. 11.8

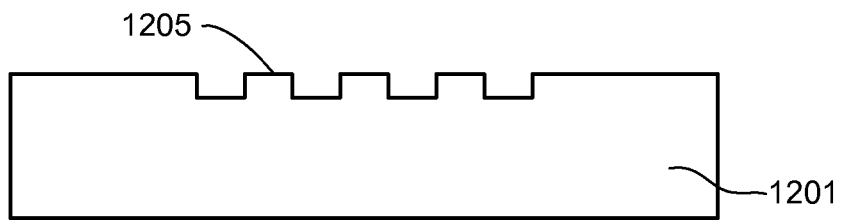
FIG. 12.1
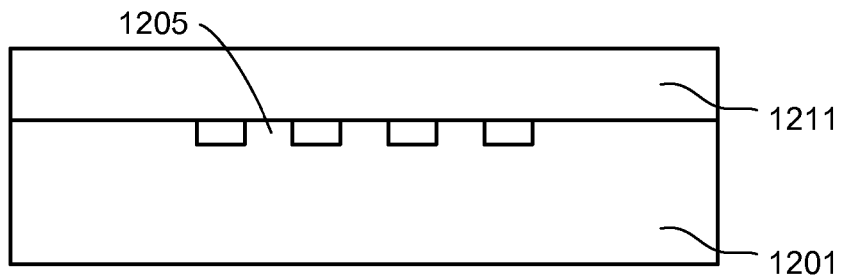
FIG. 12.2
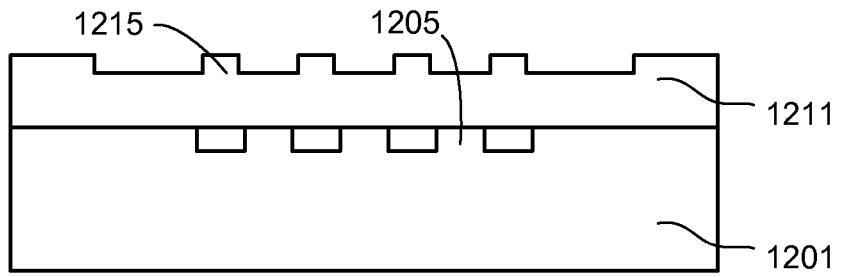
FIG. 12.3
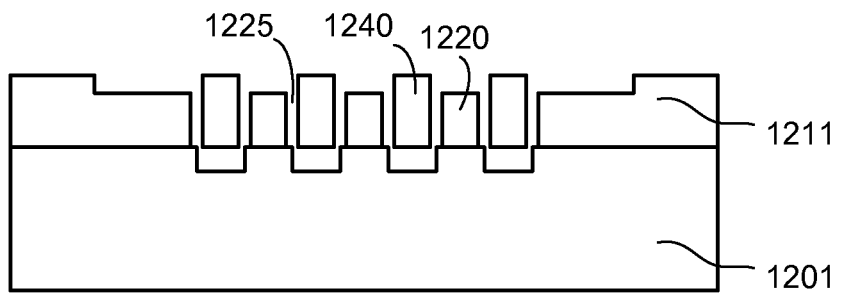
FIG. 12.4
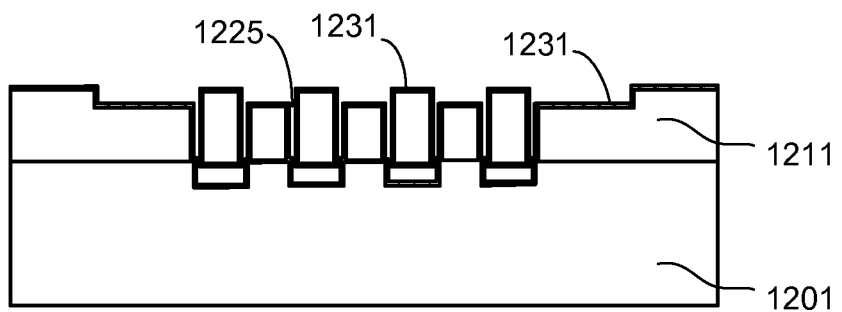
FIG. 12.5

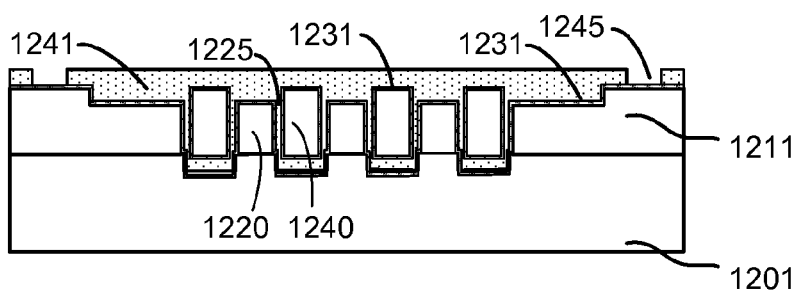
FIG. 12.6
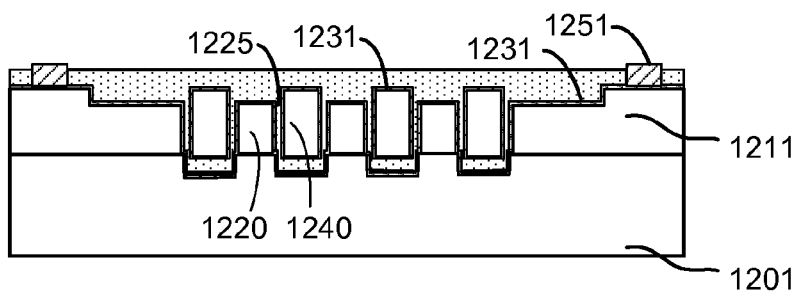
FIG. 12.7
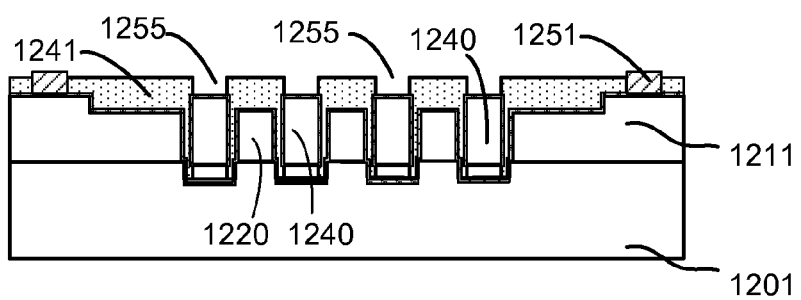
FIG. 12.8
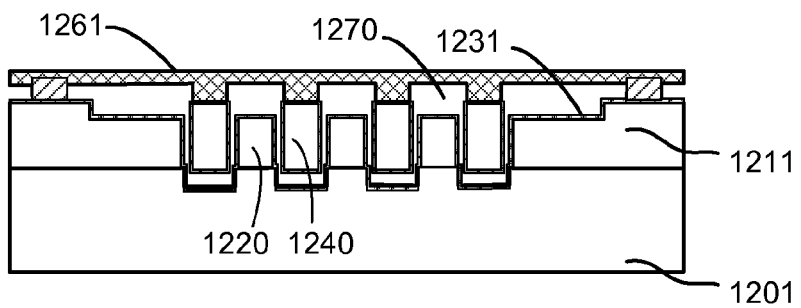
FIG. 12.9
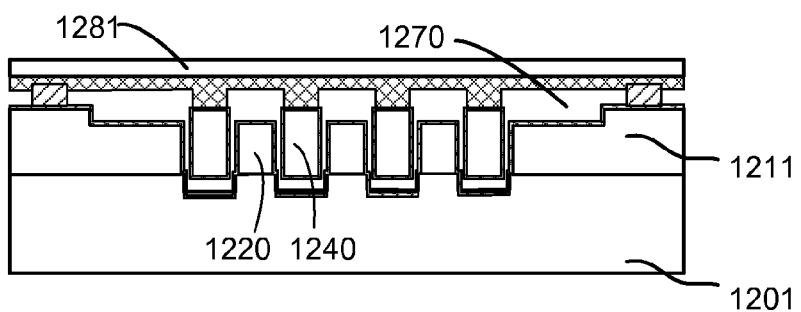
FIG. 12.10

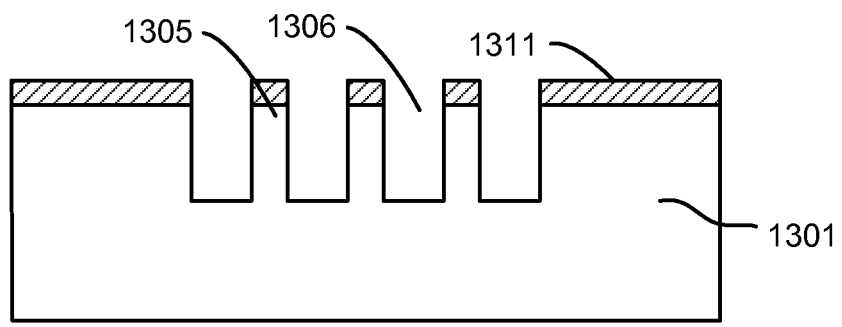
FIG. 13.1
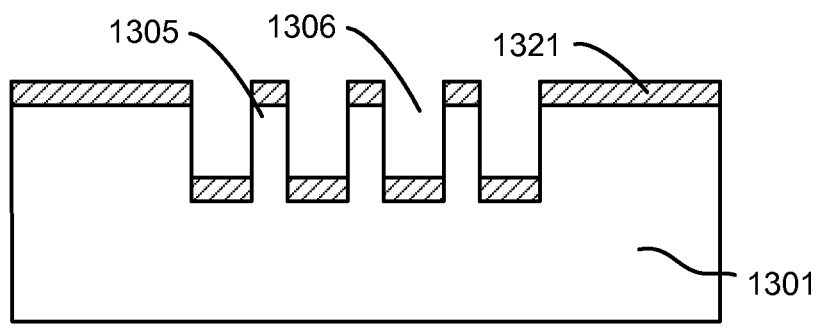
FIG. 13.2
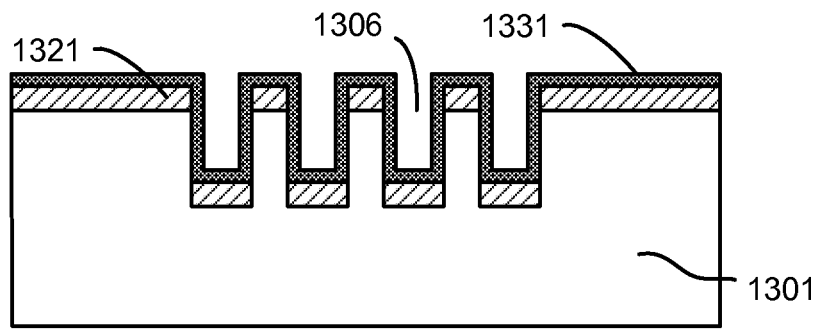
FIG. 13.3
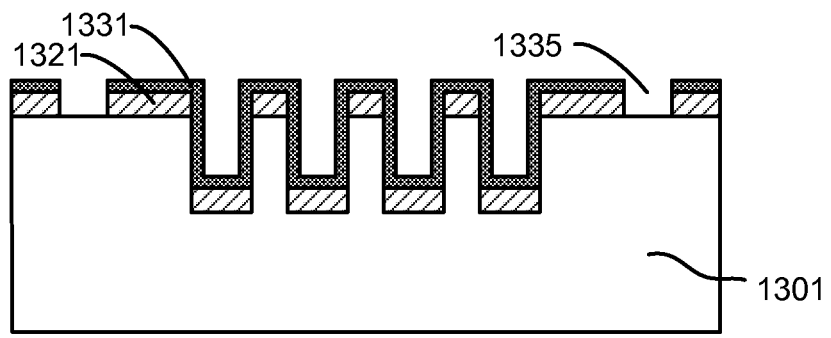
FIG. 13.4

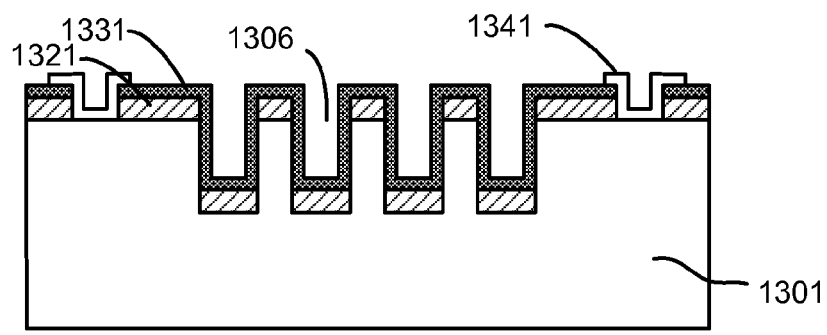
FIG. 13.5
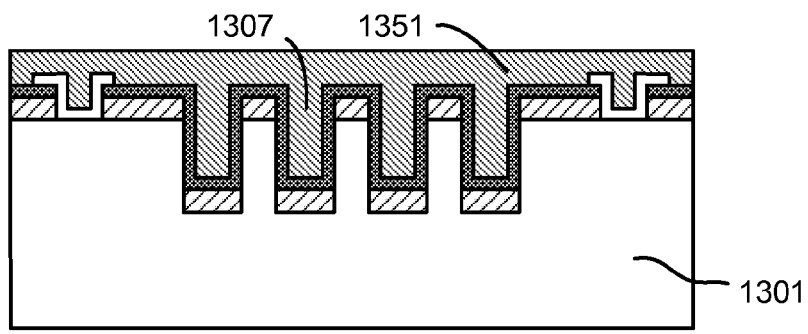
FIG. 13.6
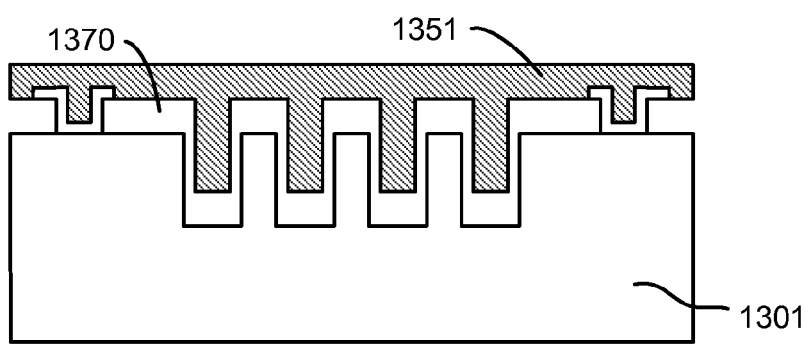
FIG. 13.7
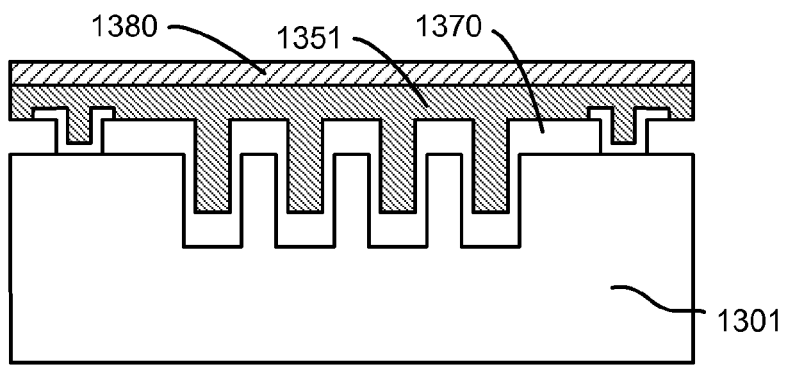
FIG. 13.8

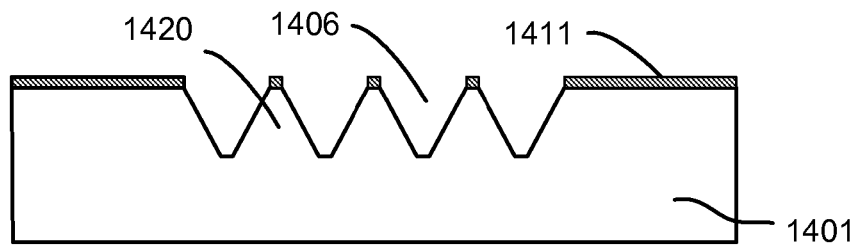
FIG. 14.1
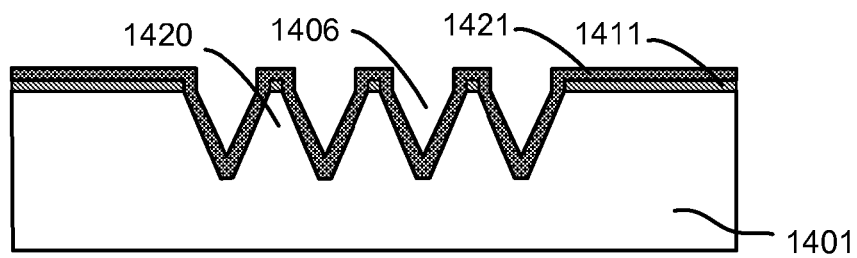
FIG. 14.2
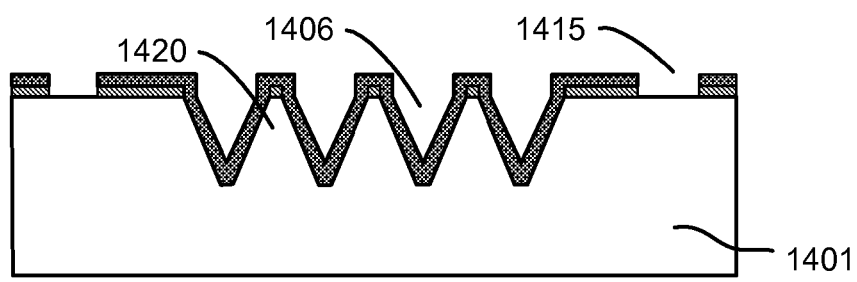
FIG. 14.3
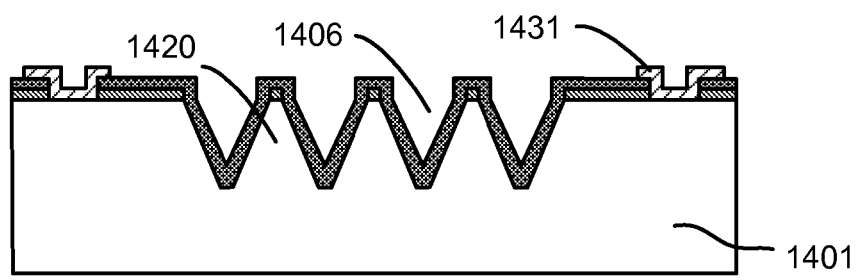
FIG. 14.4
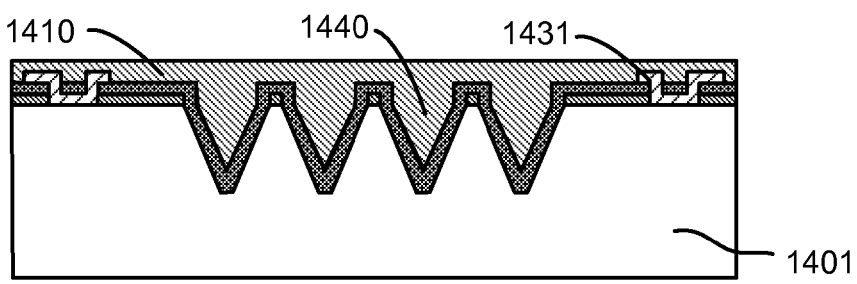
FIG. 14.5

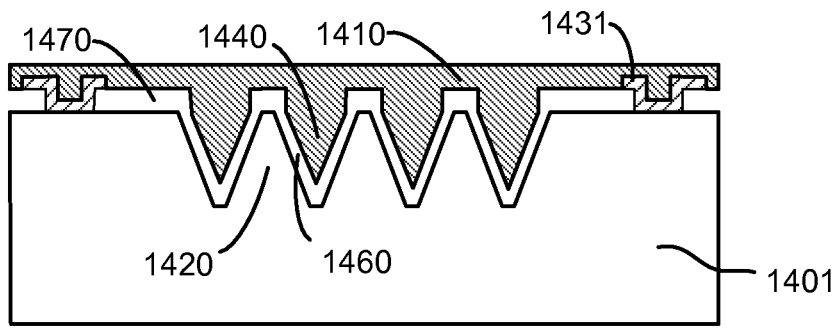
FIG. 14.6
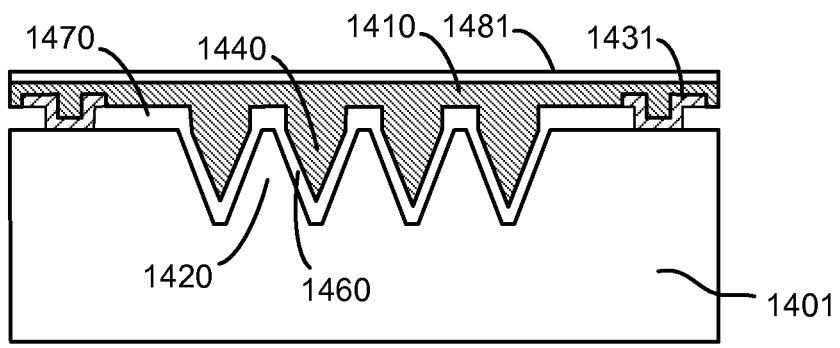
FIG. 14.7
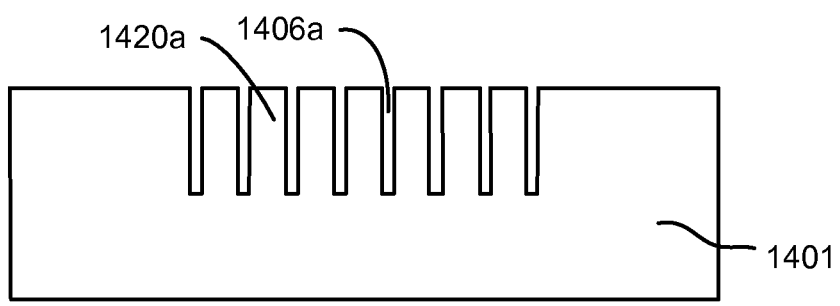
FIG. 14.1.1
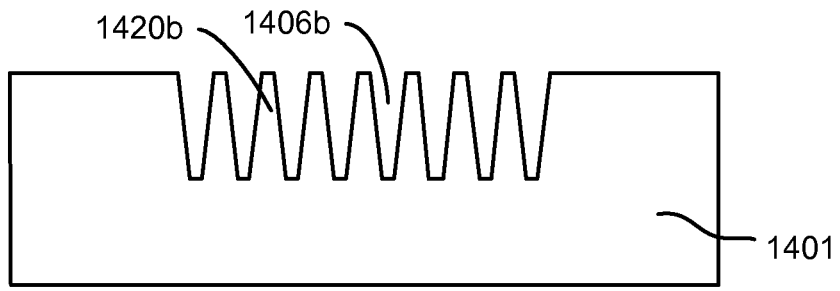
FIG. 14.1.2

US 9,132,450 B2

ELECTROSTATIC COMB DRIVER ACTUATOR/TRANSDUCER AND FABRICATION OF THE SAME

PRIORITY

This application claims priority from U.S. Provisional Application Ser. No. 60/744,242, filed Apr. 4, 2006.

This application further incorporates herein by reference in entirety the following:

International Application (PCT) No. PCT/IB2006/051567, entitled "METHODS FOR FABRICATING MICRO-ELECTRO-MECHANICAL DEVICES", filed on May 18, 2006;

International Application (PCT) No. PCT/IB2006/051568, entitled "MICRO-ELECTRO-MECHANICAL TRANSDUCERS", filed on May 18, 2006;

International Application (PCT) No. PCT/IB2006/051569, entitled "MICRO-ELECTRO-MECHANICAL TRANSDUCERS", filed on May 18, 2006; and International Application (PCT) No. PCT/IB2006/052658 entitled "MICRO-ELECTRO-MECHANICAL TRANSDUCER HAVING A SURFACE PLATE", filed Aug. 3, 2006, all by the common applicant.

BACKGROUND

The present disclosure relates to an electrostatic actuators/transducers and micro-electro-mechanical devices that have an electrostatic actuator, particularly to micromachined ultrasonic transducers (MUT) such as capacitance micromachined ultrasonic transducers (cMUT).

Electrostatic actuators/transducers are widely used in various micro-electro-mechanical system (MEMS) devices. An electrostatic actuator/transducer generally has at least two electrodes. An electrical field is applied between the two electrodes to move one or both of the electrodes or to detect the movement of the electrodes. In general, electrostatic actuators/transducers can be classified into two types: parallel plate actuators/transducers and electrostatic comb drivers.

A parallel electrostatic actuator/transducer is usually made of two electrodes which have two surfaces faces each other. At least one of two electrodes moves along the direction of applied electrical field. The electrode may move slightly off the direction of the applied electrical field if the electrode has non-uniform displacement profile. The parallel actuator/transducer is simple and occupies little space. It can usually also generate relative large electrostatic force or force density.

Parallel electrostatic actuators/transducers have been adapted to micromachined ultrasonic transducers (MUT) and used being ultrasound applications. Various parallel-types of ultrasonic transducers have been developed for transmitting and receiving ultrasound waves. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

Among the several types of MUTs, the capacitive micromachined ultrasonic transducer (cMUT), which uses electrostatic transducers, is widely used. Other MUTs using piezoelectric (pMUT) and magnetic (mMUT) transducers are also adopted.

However, parallel actuators/transducers usually have very limited displacement range. The direction of the transducer displacement is along the direction of electrical field, and the maximum displacement in this direction is limited by electrode gap g defined as the shortest distance between two electrodes even in an idea parallel plate system with a constant spring loading. When a voltage V is applied between the two electrodes, the electrostatic force $f$ generated in a unit area is $f=\in V^2/(2g^2)$, where $\in$ is the dielectric constant. The electrostatic force generated by a parallel electrostatic actuator/transducer is therefore very nonlinear as function of the electrode gap g. Moreover, a parallel plate actuator/transducer usually has a collapse voltage which further limits the displacement to only a portion, e.g. one third, of the electrode gap g.

Electrostatic comb drivers are known to have a potential to overcome the nonlinear and displacement limitations of parallel actuators/transducers. An electrostatic actuator/transducer based on a comb driver generates an electrostatic force to laterally (vertically) move a movable member of the comb driver. But the existing electrostatic comb drivers have their own challenges. For example, a comb driver usually occupies more space than that of a parallel plate actuator and has smaller electrostatic force or force density. Ideally, the width of the comb fingers should be as small as possible to enhance the force density of the comb driver. But because a certain combination of conductivity and mechanical strength is needed to maintain proper function of the comb driver, a trade-off is usually done for the design of the comb finger width.

Furthermore, electrostatic comb drivers have not been used in micromachined ultrasonic transducers, especially ultrasonic applications such as cMUTs.

SUMMARY OF THE DISCLOSURE

This application discloses electrostatic comb driver actuators/transducers. This application also discloses the fabrication methods of the same. The disclosed comb driver may be used with a variety of transducers including capacitive micromachined ultrasonic transducers (cMUT).

One aspect of the electrostatic comb driver actuator/transducer is a cMUT using a comb driver. The disclosed comb driver may be applied in both conventional membrane-based cMUT and embedded-spring cMUT disclosed in the several patent applications referenced to and incorporated herein. The comb driver cMUT has two electrodes each connected to a set of comb fingers. The two sets of comb fingers interdigitate with each other. One electrode is connected to a spring structure and movable along a vertical direction to engage and disengage the two sets of comb fingers. The movable portion is adapted to interface with a medium for ultrasonic applications.

Another aspect of the electrostatic comb driver actuator/transducer is a novel saw-toothed comb driver. The saw-toothed comb driver has two electrodes each connected to a set of saw-tooth shaped comb fingers. The two sets of saw-toothed comb fingers interdigitate with each other. One electrode is connected to a spring structure and movable along a vertical direction to engage and disengage the two sets of saw-toothed comb fingers. The movable portion is adapted to perform an actuation function and/or a sensor function. In an ultrasonic application, the mobile portion may be adapted to perform ultrasonic transmission and/or reception.

Various spring structures may be used in the disclosed electrostatic actuator/transducer. In one embodiment, the spring structure has a membrane supported by membrane supports anchored at a base portion of the electrostatic actuator/transducer. The spring structure has a membrane disposed above the movable saw-toothed comb fingers and supported by membrane supports anchored at the base portion. In other embodiments, the comb driver is implemented in embedded-spring micromachined ultrasonic transducers (ESMUT or ESCMUT). In one embodiment, for example, the spring structure comprises a spring layer disposed below the stationary comb fingers and supported by a spring anchor connected to the base portion, and the movable comb fingers are connected to a support plate which is connected to the spring layer through spring-plate connectors.

The actuator/transducer and cMUT may be fabricated using the novel fabrication methods described herein, but may also be fabricated using any other suitable methods. Particularly, some embodiments of cMUT designs of the present disclosure may be fabricated using similar methods for making micromachined ultrasonic transducers, such as the methods disclosed in the several patent applications referenced to and incorporated herein.

BRIEF DESCRIPTION OF THE DRAWINGS

FIG. 11 shows a process to make a cMUT with a comb driver.

FIG. 12 shows a second process to make a cMUT with a comb driver.

FIG. 13 shows a third process to make a cMUT with a comb driver.

FIG. 14 shows a process to make a cMUT with the saw-toothed comb driver.

DETAILED DESCRIPTION

Figure 1:
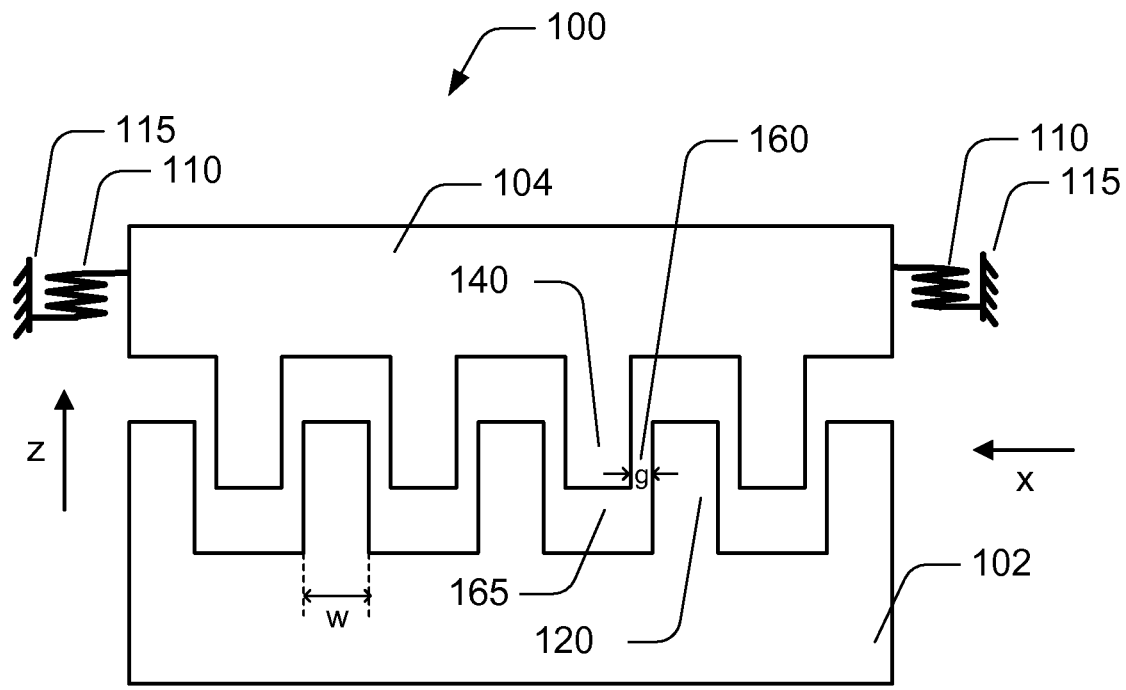
FIG. 1 is a schematic cross-sectional view of a cMUT/ESCMUT having a comb driver with a spring structure.

The electrostatic comb driver actuator/transducer for electrostatic actuation and detection will be described in detail along with the figures, in which like parts are denoted with like reference numerals or letters.

Embodiments of the electrostatic actuators/transducer are described below. In most cases, a cMUT structure is used to illustrate. It is appreciated, however, that the present disclosure is not limited to cMUTs. It will be apparent to those skilled in the art that various modifications may be made and other embodiments can be used without departing from the broader scope of the disclosure. Therefore, these and other variations upon the specific embodiments are intended to be covered by the present disclosure. Those skilled in the art will recognize that various features disclosed in connection with the embodiments may be used either individually or jointly.

It is noted that the terms "transducer" and "transducing member" are used in a broad sense in the present description to not only include devices that perform both actuation and sensing functions but also include devices that perform either an actuation function or an sensing function.

In this document, a conductive material is defined as one having a resistivity less than $1 \times 10^4$ Ω-cm. Silicon and polysilicon materials are therefore considered conductive materials in this context. A good conductive material preferably has a resistivity less than 1 Ω-cm. The terms "insulation material", "insulating material" and "dielectric material" are used interchangeably unless noted otherwise, and are defined as one having a resistivity greater than $1 \times 10^4$ Ω-cm. A good insulation/insulating material preferably has a resistivity greater than $1 \times 10^8$ Ω-cm. An insulator generally comprises an insulating material but in special cases may include air and vacuum.

Comb Driver cMUT and ESCMUT

One aspect of the electrostatic comb driver actuator/transducer is a cMUT using a comb driver. The disclosed comb driver may be applied in both conventional membrane-based cMUT and embedded-spring cMUT disclosed in the several patent applications referenced to and incorporated herein.

The basic configuration of the comb driver cMUT and comb driver is illustrated as follows.

FIG. 1 is a schematic cross-sectional view of a comb driver cMUT/ESCMUT 100 which includes a bottom electrode 102 and a top electrode 104. The bottom electrode 102 has a first set of comb fingers 120 connected thereto. The top electrode 104 has a second set of comb fingers 140 connected thereto. Comb fingers 120 and 140 interdigitatedly engage with each other to form a comb driver. The top electrode 104 including the second set of comb fingers 140 is supported by spring structures 110 which are anchored to spring anchors 115. Preferably, the spring anchors 115 and the bottom electrode 102 are connected to a common substrate (not shown). The bottom electrode 102 may be a part of the substrate, or a separate conductive layer attached to the substrate. A movable top plate (not shown) may be connected to the top electrode 104 to interface with an outside medium. Alternatively, the top electrode 104 itself may act as a movable top plate to interface with outside medium. For example, the top electrode 104 and/or a movable top plate may be adapted to interface with an ultrasonic medium for ultrasonic transmission and reception operations. For such operations, the spring structures 110, the movable top plate, and the top electrode 104 together with the movable comb fingers 140 are designed to have an operating frequency range that is suitable for ultrasonic transmission and reception operations.

As shown in electrostatic comb driver cMUT/ESCMUT 100, comb fingers 120 may be considered a part of the bottom electrode 102, and comb fingers 140 may be considered a part of the top electrode 104. Comb fingers 120 and comb fingers 140 have substantially straight vertical sides. As comb fingers 120 and comb fingers 140 interdigitate each other with the straight vertical sides facing each other in parallel to define transducing spacing 160. The width of the transducing space 160 is represented by gap g, defined as the distance between the opposing surfaces of two oppositely positioned comb fingers 120 and 140. Space 165 between two electrodes 102 and 104 at the end of each comb finger 120/140 is designed to be large enough so that the electrostatic field in space 165 generates negligible force and minimal impact on the device performance.

The electrostatic force $f$ generated in comb driver is $f=\in wV^2/(2g)$, which is perpendicular to the electrical field between comb fingers 120 and 140, where $\in$ is dielectric constant, w is the width of the comb fingers, V is the voltage, and g is the gap (width) of the transducing space 160. When the electrical field is in x-direction, the electrostatic force $f$ is in z-direction. This force is caused by asymmetrical distribution of the electrical field around the movable comb finger 140. Because the movable comb fingers 140 are connected to springs 110 which are anchored by spring anchors 115, there is a spring force applied to the movable comb fingers 140 generally in the z-direction. In addition, when the comb driver cMUT/ESCMUT 100 is at a level position, the movable comb fingers 140 and other attached components (e.g., top electrode 104) together also experience gravity, which is usually insignificant in micromachined ultrasonic transducers. These forces together determine the motion dynamics (or equilibrium in a stationary condition) of the movable comb fingers 140.

In comb driver cMUT/ESCMUT 100, the movable comb fingers 140 are displaced in the z-direction to engage or disengage the second set of comb fingers 140 from the first set of comb fingers 120. This displacement direction is perpendicular to the direction of applied electrical field in the active region of the comb driver to effectuate ultrasonic actuation and ultrasonic reception. The gap g does not change during the displacement, and therefore the electrode force is a constant and the device operates more linearly than parallel cMUT. In addition, the displacement of the device is no longer limited by the gap g.

It should be noted that comb fingers 120 are not required to have identical sizes. Likewise, comb fingers 140 are not required to have identical sizes.

From the above basic configuration, a variety of cMUT and ESCMUT may be designed using different configurations of the spring structures 110. The structures shown in FIGS. 2-4 below are examples of such designs. In addition to the variation of the basic units of the cMUT and ESCMUT structure, various cMUT/ESCMUT elements each having multiple basic units, and cMUT/ESCMUT devices each having multiple cMUT/ESCMUT elements may be designed according to different arrangements of the basic units, as described in the several patent applications referenced to and incorporated herein.

Figure 2:
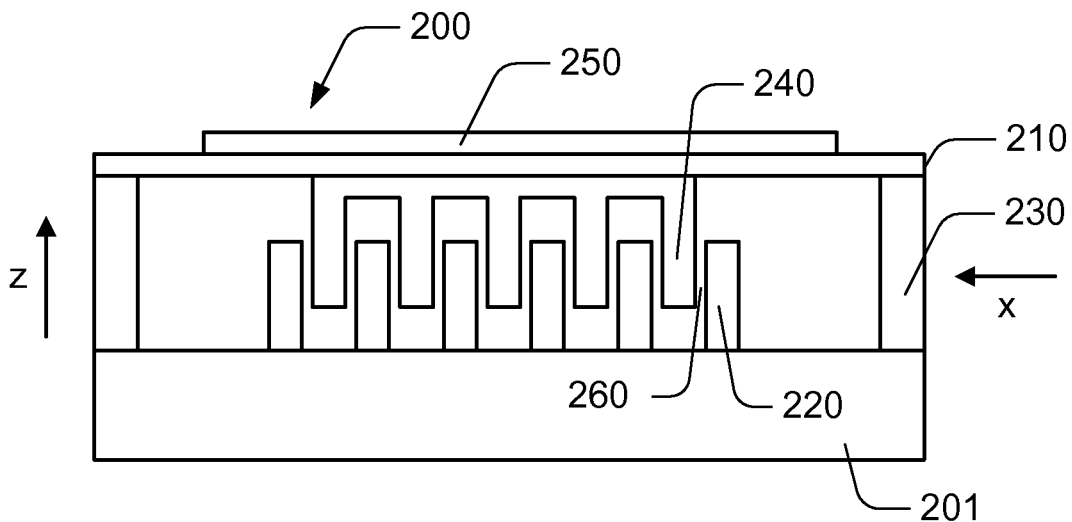
FIG. 2 is a schematic cross-sectional view of a membrane-based cMUT with a comb driver.

FIG. 2 is a schematic cross-sectional view of an exemplary membrane-based cMUT with a comb driver. The comb driver cMUT 200 has substrate 201, which may have a conductive portion (or a conductive layer attached thereto) serving as a bottom electrode; membrane 210 supported on substrate 201 by membrane supports 230; a first set of comb fingers 220 electrically connected to the bottom electrode which is attached to (not shown) or an integral part of substrate 201; a second set of comb fingers 240 attached to (or being an integral part of) membrane 210; and top electrode 250 attached to membrane 210.

The membrane 210 is disposed above the second set of comb fingers 240 and also above membrane supports 230 which are anchored to substrate 201. The second set of comb fingers 240 are electrically connected to the top electrode 250, and may be considered a part of the top electrode 250. If membrane 210 is conductive, top electrode 250 may be an integral part of membrane 210. If membrane 210 is not conductive, it is then operatively preferable to electrically connect the top electrode 250 with the second set of comb fingers 240 through holes on the membrane 210.

Membrane 210 is spaced from substrate 201 to make room for common fingers 220 and 240. The first set of comb fingers 220 and the second set of comb fingers 240 interdigitate with each other with adjacent comb fingers 220 and 240 facing each other and separated in the x-direction by a narrow space 260. The first set of comb fingers 220 may be substantially stationary with substrate 201, while the second set of comb fingers 240 are movable in the vertical z-direction due to the flexibility of membrane 210. When a voltage is applied to one of the two sets of comb fingers 220 and 240 with respect to the other, asymmetrical distribution of electrical field lines around each comb finger 220 or 240 results in an electrostatic force in the z-direction to move the second set of comb fingers 240 upward in that direction. Because the movable comb fingers 240 are attached to membrane 210 which is anchored through membrane supports 230 to substrate 201, there is a spring force applied to the movable comb fingers 240 generally in the z-direction. These forces together determine the motion dynamics (or equilibrium in a stationary condition) of the movable comb fingers 240.

In transmission mode, an electrical input signal is applied as a voltage signal across the first set of comb fingers 220 and the second set of comb fingers 240 in x-direction. The variation of electrical input signal generates a z-direction displacement of the movable comb fingers 240, and further that of membrane 210 (and top electrode 250 if applicable) to interface with a medium (not shown). At a proper frequency range, this motion generates ultrasonic waves in the medium.

In reception mode, a reverse process takes place. Ultrasonic waves in the medium drive the membrane 210 and the movable comb fingers 240, the motion of which then generates an output electric signal detected by a reception circuit (not shown). Specifically, the z-direction displacement of the movable comb fingers 240 causes a change of the capacitive area (an overlapping area) between the two sets of comb fingers 220 and 240 and thus results in a variation of the capacitance formed therebetween. The variation of the capacitance is detected by the reception circuit in a manner similar to that in conventional cMUT.

The comb driver cMUT 200 is distinct from the conventional parallel plate cMUT, which does not have a comb driver with comb fingers but instead has a flat bottom electrode and a flat top electrode interface in with each other directly. The comb driver cMUT 200 is potentially more linear than parallel plate cMUT, especially in transmission (TX) operation which involves large displacement. In addition, the z-direction displacement of the comb driver cMUT 200 is not limited by the minimum electrode gap g (e.g., the gap defined by the narrow space 260 between two adjacent comb fingers 220 and 240) in the comb driver. The comb driver cMUT 200 may also be able to more easily avoid transducer collapse and is therefore more reliable. Furthermore, there is less need for insulation as the electrodes including the comb fingers 220 and 240 are less likely to contact each other during the operation of the comb driver cMUT 200.

In addition to applications in the conventional membrane-based cMUT as shown in FIG. 2, the disclosed comb driver may be applied in embedded-spring cMUT (ESCMUT) disclosed in the several patent applications referenced to and incorporated herein, thus taking advantage of the benefits of both ESCMUT and comb drivers.

Figure 3:
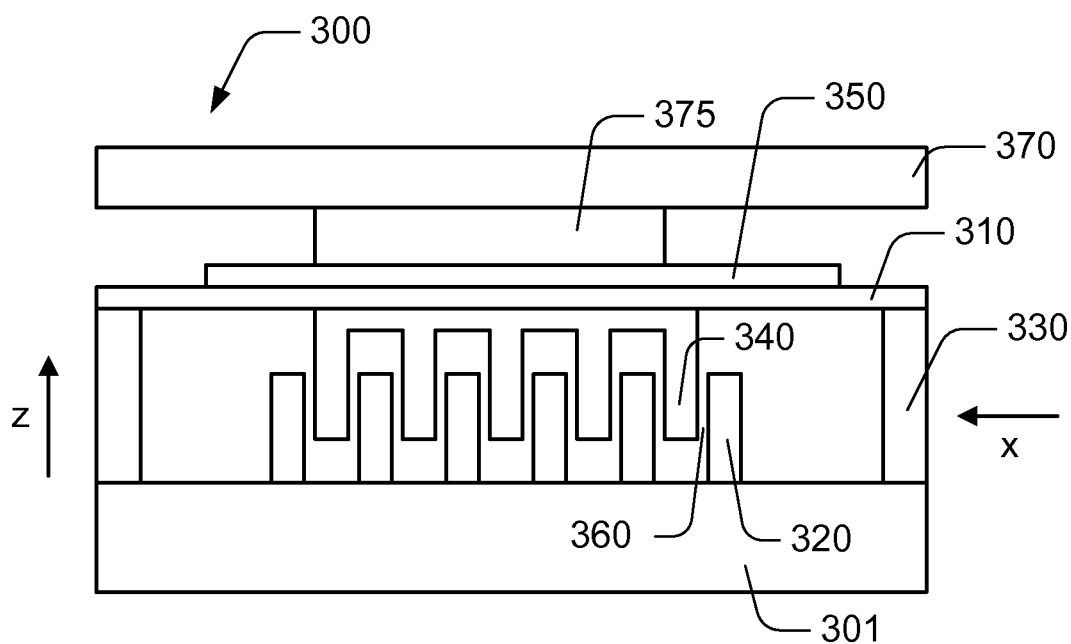
FIG. 3 is a schematic cross-sectional view of an embedded-spring cMUT (ESCMUT) with a comb driver.

FIG. 3 is a schematic cross-sectional view of an embedded-spring cMUT (ESCMUT) with a comb driver. The comb driver cMUT 300 is based on an ESCMUT disclosed in PCT International Application PCT/IB2006/052658 entitled "MICRO-ELECTRO-MECHANICAL TRANSDUCER HAVING A SURFACE PLATE", filed august 3, 2006 by the common applicant, particularly the ESCMUT shown in FIG. 4 therein. The comb driver cMUT 300 is only part of a complete cMUT element (not shown).

The comb driver cMUT 300 includes substrate 301, which may either serve as a bottom electrode or has an attached conductive layer (not shown) as a bottom electrode. A first set of comb fingers 320 are connected to the substrate 301 and electrically connected to the bottom electrode. A second set of comb fingers 340 are connected to a spring layer 310 (e.g., a flexible membrane), which is disposed above the second set of comb fingers 340 and is connected to the substrate 301 through spring anchors 330. A top electrode 350 is placed on the spring layer 310. The second set of comb fingers 340 are preferably electrically connected to the top electrode 350, and may be considered a part of the top electrode 350. If the spring layer 310 is made of a conductive material to serve as the top electrode, a separate top electrode 350 may not be needed.

The first set of comb fingers 320 and the second set of comb fingers 340 interdigitate with each other with adjacent comb fingers 320 and 340 facing each other and separated by a narrow space 360 in the x-direction. The first set of comb fingers 320 may be substantially stationary with substrate 301, while the second set of comb fingers 340 are movable in the vertical z-direction due to the flexibility of membrane 310.

Similar to the comb driver cMUT/ESCMUT 100 in FIG. 1, when a voltage is applied to one of the two sets of comb fingers 320 and 340 with respect to the other, an asymmetrical distribution of electrical field lines results in an electrostatic force in the z-direction to move the second set of comb fingers 340 upward in that direction. Because the movable comb fingers 340 are attached to spring layer 310 which is anchored through spring anchors 330 to substrate 301, there is a spring force applied to the movable comb fingers 340 generally in the z-direction. The electrostatic force, spring force, and gravity together determine the motion dynamics (or equilibrium in a stationary condition) of the movable comb fingers 340.

A surface plate (mass layer) 370 is connected to the top electrode 350, and thus to the spring layer 310, through spring-mass connector 375. The surface plate 370 may be adapted to interface with a medium. The surface plate 370 is actuated by the applied electrode field between two sets of comb fingers 320 and 340 to transmit the ultrasound into the medium; and reversely the ultrasound can be detected if it impinges on the surface plate 370 to cause the capacitance between two sets of comb fingers 320 and 340 to change. The surface plate 370 increases the equivalent mass and spring constant in the transducer, and thus may affect the operating frequency of the transducer.

The cMUT may be operated in two different modes. In a reception mode, ultrasonic waves in a medium is picked up by the surface plate 370 which moves in a piston fashion to exert a force on the spring layer 310 through the spring-mass connector 375. The spring layer 310 is anchored at its two ends at spring anchors 330. When pushed by the surface plate 370 through the spring-mass connectors 375, the spring layer 310, the top electrode 350, and the second set of comb fingers 340 move relative to the bottom electrode (on the substrate 301) and the first set of comb fingers 320, causing a change in the capacitance of the capacitor formed between the two sets of comb fingers 320 and 340. The capacitance change is picked up by the device circuitry as the signal.

In a transmitter mode, the movable comb fingers 340 are driven by the electrostatic force of the asymmetrical electrical field created by the device circuitry to cause a motion of the top electrode 350. The motion of the top electrode 350 moves the surface plate 370, which interfaces with the surrounding medium to transmit an ultrasound signal.

The comb driver cMUT 300 may be only a portion of a single ESCMUT in practice. Despite the similarity between the lower parts of the comb driver cMUT 300 and the comb driver cMUT/ESCMUT 100, they may have very different overall structure as described in the patent applications referenced and incorporated herein. In the ESCMUT, a single ESCMUT element may have multiple spring units that are mechanically connected by a common surface plate and therefore coupled to each other during the transducer operation. This fundamental difference results in a different spring system. As a result, the comb driver cMUT 200 and the comb driver cMUT 300 may be two essentially different physical structures when the transducer or a transducer element is viewed as a whole. The two different structures may have significantly different frequency response and mode shapes even if they may have basic units that look alike individually in a schematic cross-sectional view. Moreover, the basic units in ESCMUT do not need to be identical.

The surface plate (mass layer) 370 may preferably a contiguous plate moving as a single mechanical member for each ESCMUT element. Using a contiguous plate (which may nevertheless have patterns such as holes and a honeycomb structure in some embodiments to enhance the rigidity/mass ratio) for each element may be benefiting for keeping a unified phase within the same cMUT element. However, multiple segments of the surface plate 370 may also be used. The surface plate 370 is preferably light and rigid.

Figure 4:
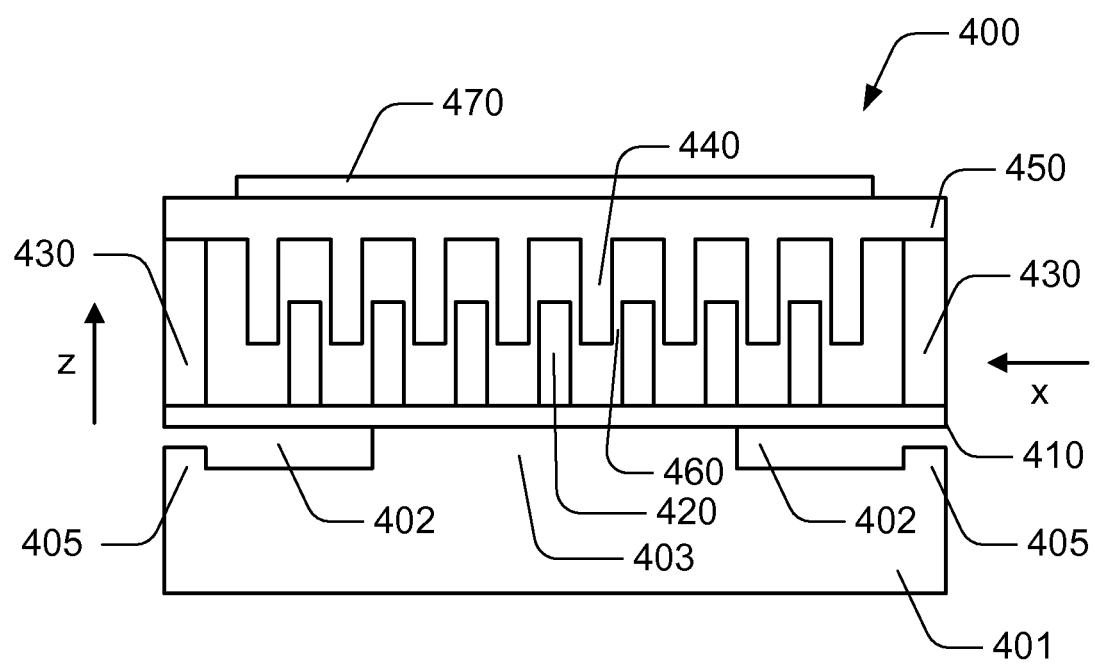
FIG. 4 is a schematic cross-sectional view of another embedded-spring cMUT (ESCMUT) with a comb driver.

FIG. 4 is a schematic cross-sectional view of another embedded-spring cMUT (ESCMUT) with a comb driver. The comb driver cMUT 400 is based on an ESCMUT disclosed in the incorporated PCT International Application No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006, particularly the ESCMUT shown in FIGS. 5A-5D therein. The comb driver cMUT 400 is only a part of a complete ESCMUT element (not shown).

The comb driver cMUT 400 has a substrate 401, on top of which are spring anchor 403 having two sidewalls on two opposing sides bordering cavities 402 and motion stoppers 405. The spring anchor 403 and motion stoppers 405 may be an integrated part of the substrate 401 formed as a result of forming the cavities 402, but may also be additional structures added onto the separate substrate 401. The substrate of 401 may be made of either a nonconductive material or a conductive material such as silicon or polysilicon.

The comb driver cMUT 400 further has these components: a spring layer 410 which is preferably an elastic membrane; a first set of comb fingers 420 connected to the spring layer 410; a surface plate 450 connected to the spring layer 410 through spring-plate connectors 430; a second set of comb fingers 440 connected to the surface plate 450; and a top electrode 470 connected to the surface plate 450.

The two sets of comb fingers 420 and 440 interdigitate with each other to form a comb driver. Adjacent comb fingers 420 and 440 face each other to define a narrow space 460 in the x-direction. The first set of comb fingers 420 may be substantially stationary with substrate 401, while the second set of comb fingers 440 are movable in the vertical z-direction due to the flexibility of spring layer 410 which forms a springy cantilever anchored at spring anchor 403. Similar to the comb driver cMUT 200 in FIG. 2 and the comb driver cMUT 300 in FIG. 3, when a voltage is applied to one of the two sets of comb fingers 420 and 440 with respect to the other, an asymmetrical distribution of electrical field lines results in an electrostatic force in the z-direction to move the second set of comb fingers 440 upward in that direction. Because the movable comb fingers 440 are attached to spring layer 410 which is anchored through spring anchors 403 to substrate 401, there is a spring force applied to the movable comb fingers 440 generally in the z-direction. The electrostatic force and spring force together mostly determine the motion dynamics (or equilibrium in a stationary condition) of the movable comb fingers 440.

Unlike the membrane 210 in FIG. 2 and the spring layer 310 in FIG. 3, the spring layer 410 is disposed under, rather than above, comb fingers 420 and 440. Furthermore, the movable comb fingers 440 are connected to surface plate 450 instead of to the spring layer 410 directly. The surface plate 450 acts as a support plate to support the movable comb fingers 440.

The first set of comb fingers 420 are preferably electrically connected to a bottom electrode, which may be served by the spring layer 410 or the spring anchor 403 if either of which is made of a conductive material, or served by a separate conductive layer (not shown) connected to the spring layer 410. If so connected, the first set of comb fingers 420 may be considered a part of the bottom electrode. The second set of comb fingers 440 are preferably electrically connected to the top electrode 470, and if so connected, may be considered a part of the top electrode 470. If the surface plate 450 is nonconductive, holes may need to be made on the surface plate 450 in order to accommodate the electrical connection between the second set of comb fingers 440 and the top electrode 470.

The comb driver cMUT 400 may be only a portion of a complete ESCMUT element (not shown). Depending on how and where the comb driver cMUT 400 is taken from the complete ESCMUT element, the two cavities 401 shown in FIG. 4 may either belong to a different and separate cavity, or just two portions of a same circular or extended cavity. Likewise, depending on how and where the comb driver cMUT 400 is taken from a complete ESCMUT element, the two spring-plate connectors 430 may either each be a part of a different and separate connector, or just two portions of the same circular or extended connector.

The comb drivers shown in FIGS. 1-4 promise better linearity in operation, less restriction on maximum displacement, and better reliability. However, these comb drivers may occupy more room than a parallel cMUT and also have smaller electrostatic force or force density. Ideally, the width of comb finger should be as small as possible to enhance the force density of the transducer. However, in order to maintain proper function of the comb driver, both conductivity and mechanical strength may need to meet certain conditions. As a result, trade-offs may need to be done for the design of the comb finger width. Some of these issues may be addressed by a saw-toothed electrostatic comb driver described below.

Saw-Toothed Electrostatic Comb Driver

Another aspect of the electrostatic comb driver actuator/transducer is a novel saw-toothed comb driver to replace the comb drivers having straight vertical comb fingers shown in FIGS. 1-4.

Figure 5:
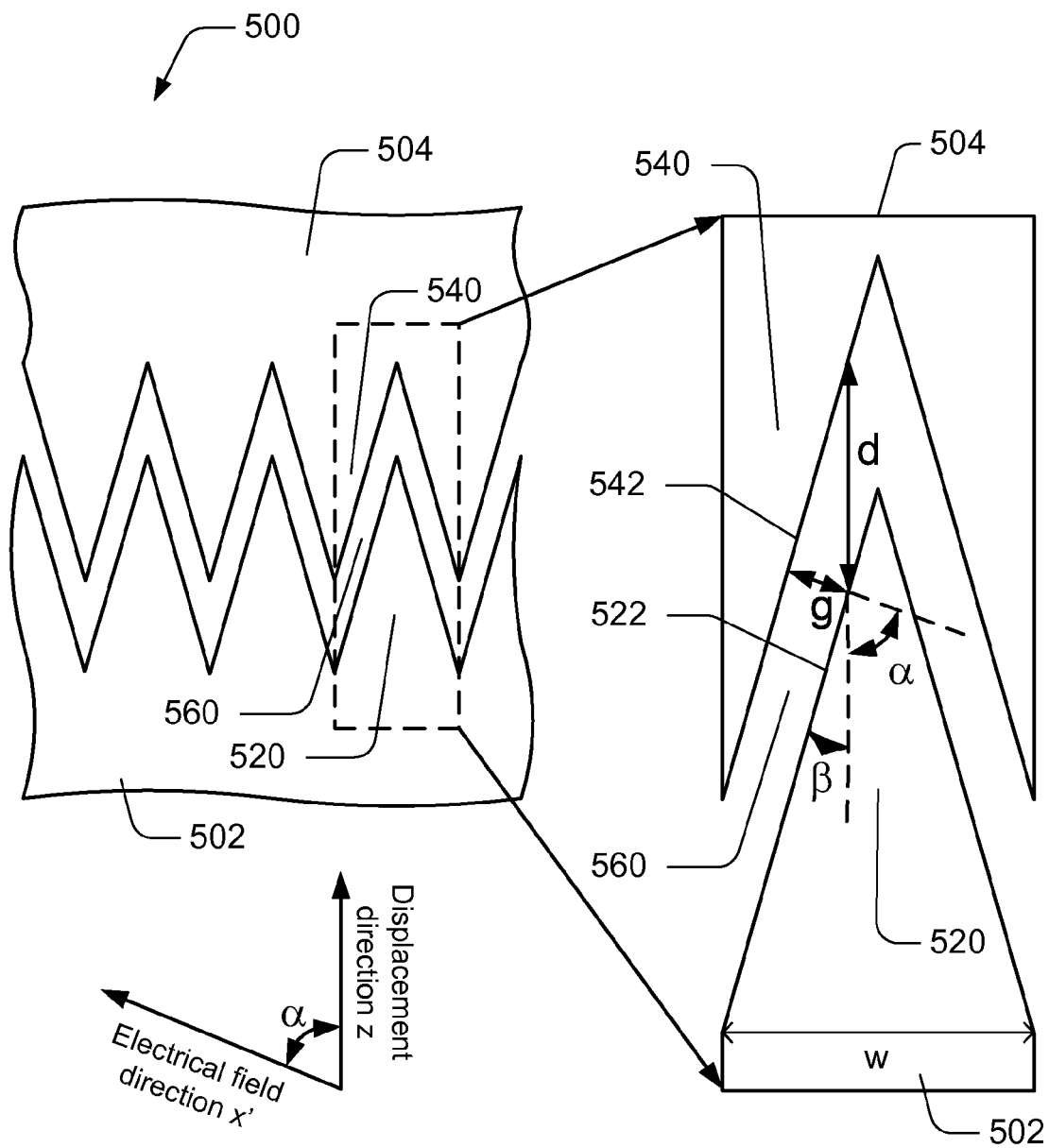
FIG. 5 is a schematic cross-section view of a saw-toothed electrostatic comb driver.

FIG. 5 is a schematic cross-section view of a saw-toothed electrostatic comb driver 500 which includes a bottom electrode 502 and a top electrode 504. The bottom electrode 502 has a first set of saw-tooth shaped comb fingers 520 connected thereto. The top electrode 504 has a second set of saw-tooth shaped comb fingers 540 connected thereto. Saw-tooth shaped comb fingers 520 and 540 interdigitate with each other to form a comb driver.

A portion of the saw-toothed electrostatic comb driver 500 is enlarged to show detail in a zoomed widow on the right side in FIG. 5. As shown, the comb finger 540 is saw-tooth shaped with at least one side skewed from the z-direction, and likewise the comb finger 520 is saw-tooth shaped with at least one opposing side skewed from the z-direction facing the skewed side of the comb finger 540. Preferably, the two opposing skewed sides of the comb finger 540 and 524 are substantially parallel to each other, forming an identical or similar skew angle ($\beta$) with the displacement direction. With this configuration, the comb finger 520 and the comb finger 540 conformally engage with each other. The skew angle $\beta$ is in the range of $0°<\beta<90°$, and preferably in a range of $10°<\beta<80°$.

The saw-tooth shaped comb fingers 520 and 540 may be considered as a part of the electrodes 502 and 504 respectively. The interdigitatedly engaged saw-tooth shaped comb fingers 520 and 540 have a desired separation between respective front surfaces opposing each other. The separation between the saw-tooth shaped comb fingers 520 and 540 defines transducing space 560. The shortest distance between the two electrodes 502 and 504 is the distance between two opposing saw-tooth shaped comb fingers 520 and 550 measured by gap g. The distance between two electrodes 502 and 504 measured in the direction of the displacement of the comb driver 500 is measured by vertical displacement d.

The front surfaces 522 and 542 of the saw-tooth shaped comb fingers 520 and 540 face each other to form an active region of the saw-toothed electrostatic actuator/transducer 500. Unlike the straight vertical comb drivers in FIGS. 1-4, front surfaces 522 and 542 are set at an angle $\beta$ from the displacement direction of the device. The direction of local electrical field in the device active region is perpendicular to the opposing front surfaces 522 and 542 and thus forms an angle of $\alpha$ ($\alpha=90°-\beta$) with the direction of the device displacement.

Collectively, the movable electrode (e.g., top electrode 504) experiences an electrostatic force $f=\in V^2/(2g^2)$ along the displacement direction of the device. This electrostatic force $f$ is the same as that in a parallel plate actuator for a given voltage V and gap g, and is different from the electrostatic force $f=\in wV^2/(2g)$ found in the straight vertical comb driver cMUT/ESCMUT 100 in FIG. 1. Therefore, the saw-toothed comb driver may generate an electrostatic force which is at a comparable level to that generated by the parallel plate actuator and larger than that generated by a straight vertical comb driver. Yet the saw-toothed comb driver 500 does not suffer from a nonlinearity problem as severe as that suffered by the parallel plate actuator is. Although in the saw-toothed comb driver 500 the electrostatic force has a nonlinear relationship with the gap g as in the parallel plate actuator, for a given displacement d the change in g is determined by $g=d \sin \beta$, which is smaller than d. The nonlinearity in the saw-toothed comb driver 500 is thus less sensitive to the actual displacement if a proper angle β is chosen. When the angle β is approaching 90°, the behavior of the saw-toothed comb driver 500 approaches that of a parallel plate actuator. As the angle β approaches 0°, the behavior of the saw-toothed comb driver in one sense approaches that of a straight vertical comb driver as shown in FIGS. 1-4, but in another sense never becomes one because that would require the width w of each saw-tooth shaped comb finger 520 and 540 to be infinitely small, corresponding to an infinite comb finger density. In this sense, the straight vertical comb drivers shown in FIGS. 1-4 are a different structure type than the saw-toothed comb driver 500.

Compared to the straight vertical comb driver shown in FIGS. 1-4, the displacement of the saw-toothed comb driver 500 is limited by $d=g/\sin \beta$, rather than theoretically unlimited. On the other hand, compared to the conventional parallel plate actuators, the displacement of the saw-toothed comb driver 500 may be as great as $d=g/\sin \beta$, instead of being limited to g only. Therefore, the displacement range of the saw-toothed comb driver is between that of the parallel plate and the straight vertical comb driver. The displacement range of the saw-toothed comb driver 500 can be optimally selected and may be much larger than that of the parallel plate actuator by choosing the proper angle β, while the gap g of the saw-toothed comb driver 500 may also be optimally selected to result in a much greater electrostatic force than that of straight vertical comb drivers in FIGS. 1-4. The saw-toothed comb drive 500 thus opens new dimensions of design room and flexibility.

It is noted that numerous variations may exist to the exemplary embodiment of the saw-toothed comb driver 500 show in FIG. 5 without departing the spirit of the new design. For example, a front side of each saw-tooth shaped comb fingers 520 and 540 may have a variable slope (corresponding to a variable angle β); the front sides of different saw-tooth shaped comb fingers 520 and 540 may have different skew angles β; and saw-tooth shaped comb fingers 520 and 540 may have a nonuniform size (width w), etc. In addition, the tip end of each saw-tooth shaped comb finger 520 and 540 may have a contoured shape instead of a sharp end as shown in FIG. 5. Furthermore, the saw-tooth shaped comb fingers 520 are not required to be identical in size, and each saw-tooth shaped comb finger 520 is further not required to have a symmetrical shape. Likewise, the saw-tooth shaped comb fingers 540 are not required to be identical in size, and each saw-tooth shaped comb finger 540 is further not required to have a symmetrical shape. The interdigitating saw-tooth shaped comb fingers 520 and 540 should preferably have a substantially conforming shape with respect to each other, but a close match of the shape is not required.

Figure 6:
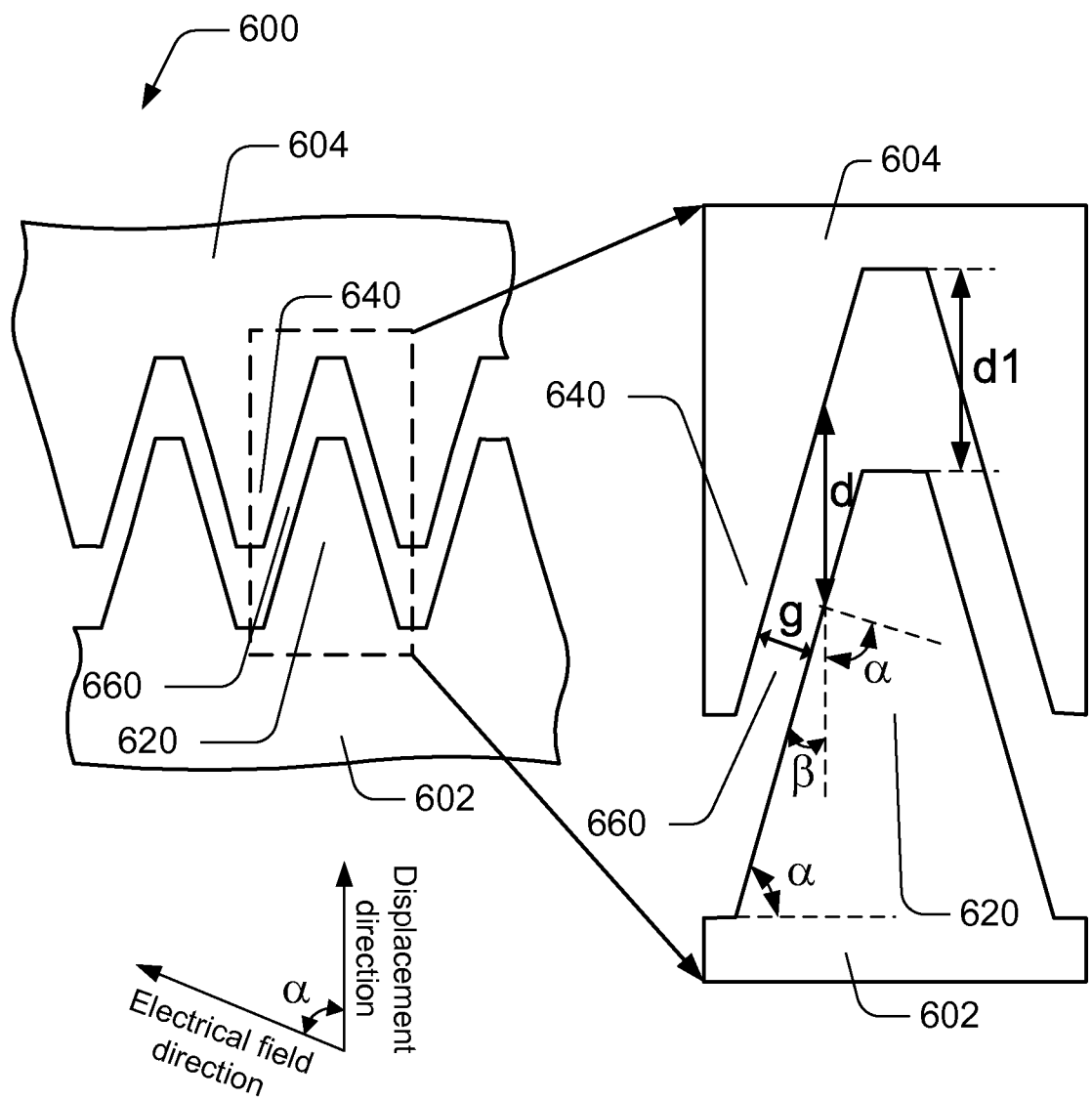
FIG. 6 is a schematic cross-section view of a variation of the saw-toothed comb driver.

FIG. 6 is a schematic cross-section view of a variation of the saw-toothed comb driver. The saw-toothed comb driver 600 is similar to the saw-toothed on driver 500 except for the shape of the tip ends of the saw-tooth shaped comb fingers. Instead of a sharp ending as shown in FIG. 5, saw-tooth shaped comb fingers 620 and 640 have a flat end with a matching flat bottom at the opposing side of the comb fingers 620 and 640. It is appreciated that any other shape, such as a rounded dome shape, may be used. A particular shape may be chosen for easier fabrication, as the sharp corners of the comb fingers 520 and 540 may be difficult to fabricate. Sharp corners may also not be desired for other particle reasons. Usually the separation $d_1$ between two electrodes 602 and 604 at the tip ends of comb fingers 620 and 640 should preferably not be smaller than $d=g/\sin \beta$ in order to avoid unnecessary restriction on the maximum displacement of the device.

Compared the parallel plate actuator and the straight vertical comb driver, the saw-toothed electrostatic comb driver provides great flexibility to balance among the electrostatic force, device displacement range and device linearity. The saw-toothed electrostatic comb drivers may be used to replace the parallel plate actuators and the straight vertical comb drivers in various actuators/transducers including but not limited to capacitive micromachined ultrasound transducers. In the following, the saw-toothed electrostatic comb driver is further illustrated using the ultrasound applications as examples.

Figure 7:
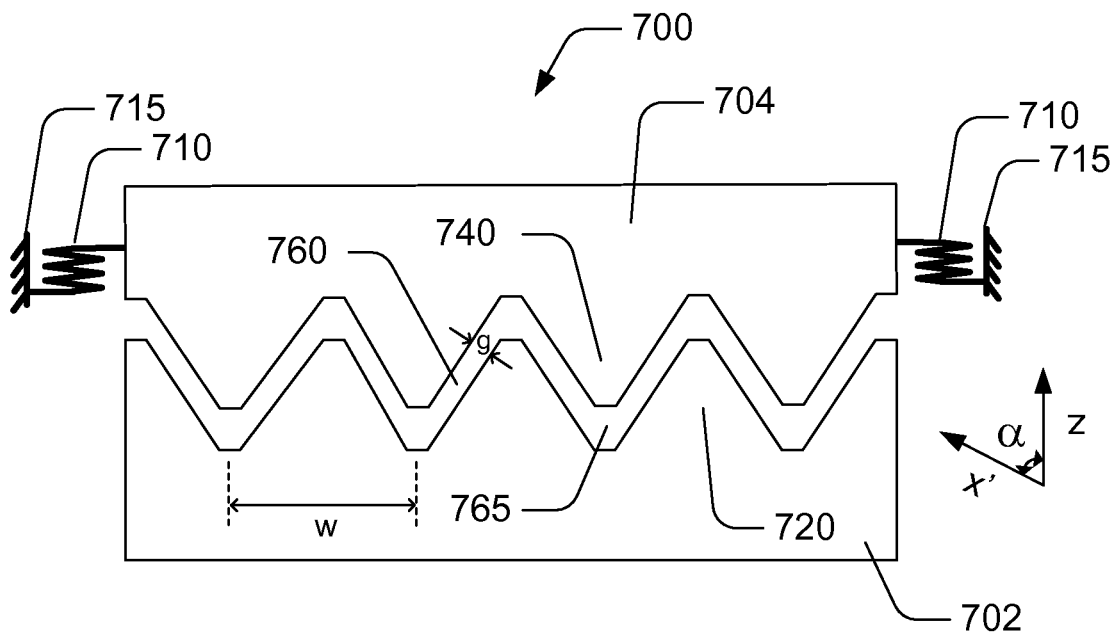
FIG. 7 is a schematic cross-sectional view of a saw-toothed comb driver with a spring structure.

FIG. 7 is a schematic cross-sectional view of an electrostatic transducer with a saw-toothed comb driver. The comb driver electrostatic transducer 700 is based on the comb driver cMUT/ESCMUT 100 in FIG. 1 but with saw-tooth shaped comb fingers replacing the straight vertical comb fingers. The saw-toothed comb driver electrostatic transducer 700 includes a bottom electrode 702 and a top electrode 704. The bottom electrode 702 has a first set of saw-tooth shaped comb fingers 720 connected thereto. The top electrode 704 has a second set of saw-tooth shaped comb fingers 740 connected thereto. Comb fingers 720 and 740 interdigitate with each other to form a comb driver.

The top electrode 704 including the second set of comb fingers 740 is supported by spring structures 710 which are anchored to spring anchors 715. Preferably, the spring anchors 715 and the bottom electrode 702 are connected to a common substrate (not shown). The bottom electrode 702 may be a part of the substrate, or a separate conductive layer attached to the substrate.

The saw-toothed comb driver electrostatic transducer 700 may be adapted to perform either an actuation function (in a transmission mode) or sensor function (in a reception mode), or both. A movable top plate (not shown) may be connected to the top electrode 704 to interface with an outside medium. Alternatively, the top electrode 704 itself may act as a movable top plate to interface with outside medium. In an ultrasonic application, the top electrode 704 and/or the movable top plate are adapted to interface with a medium for ultrasonic transmission and reception operations. The spring structures 710, the movable top plate if applicable, and the top electrode 704 together with the movable comb fingers 740 are designed to have an operating frequency range that is suitable for such ultrasonic transmission and reception operations.

As shown in electrostatic comb driver electrostatic transducer 700, comb fingers 720 may be considered a part of the bottom electrode 702, and comb fingers 740 may be considered a part of the top electrode 704. Comb fingers 720 and comb fingers 740 have skewed front sides to define a saw-toothed shape as illustrated in FIG. 6. As comb fingers 720 and comb fingers 740 interdigitate each other, the skewed front sides face each other, preferably in parallel, to define transducing spacing 760. The width of the transducing space 760 is represented by gap g, defined as the distance between the opposing surfaces of two oppositely positioned comb fingers 720 and 740.

Space 765 between two electrodes 702 and 704 at the end of each comb finger 720/740 is designed to be large enough so that the electrostatic field in space 765 generates negligible force and minimal impact on the device performance. The space 765 is also preferably designed to maximize the z-direction vertical displacement of the movable electrode 704.

In comb driver electrostatic transducer 700, the movable comb fingers 740 are displaced vertically at the z-direction, which is at an angle α with the x'-direction, which is the direction of applied local electrical field in the active region of the comb driver electrostatic transducer 700. The gap g changes during the displacement, and therefore the electrode force is not a constant and the device operates non-linearly. However, because the change of gap g is slower than the actual vertical displacement due to the angle $\beta=90°-\alpha$, the saw-toothed comb driver electrostatic transducer 700 operates more linearly than a parallel actuators/transducer.

Based on the above basic comb driver configuration, a variety of electrostatic actuators/transducers, such as cMUT and ESCMUT, may be designed using different configurations of the structural components, particularly that of the spring structures 710. The structures shown in FIGS. 8-10 below are examples of such designs. In addition to the variation of the basic structural units of the actuator/transducer structure, various actuator/transducer elements each having multiple basic units, and actuator/transducer devices each having multiple actuator/transducer elements, may be designed according to different arrangements of the basic units, as described in the several patent applications referenced to and incorporated herein.

Figure 8:
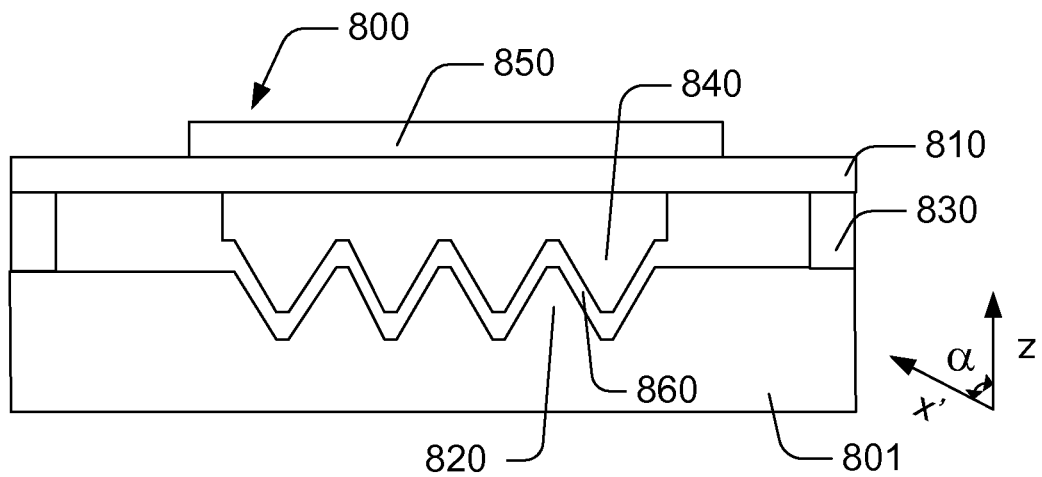
FIG. 8 is a schematic cross-sectional view of a membrane-based electrostatic actuator/transducer with a saw-toothed comb driver.

FIG. 8 is a schematic cross-sectional view of a membrane-based electrostatic actuator/transducer with a saw-toothed comb driver. The saw-toothed comb driver electrostatic transducer 800 is similar to the comb driver cMUT 200 in FIG. 2 except that the comb driver actuator/transducer 800 has saw-toothed comb fingers 820 and 840 instead of the straight vertical comb fingers 220 and 240 in the comb driver cMUT 200. The structure of saw-toothed comb driver electrostatic transducer 800 therefore may be understood in a similar way as the comb driver cMUT 200 in FIG. 2. The comb driver electrostatic transducer 800 has the benefit of a saw-toothed comb driver as discussed above.

The comb driver electrostatic transducer 800 has substrate 801, which may have a conductive portion (or a conductive layer attached thereto) serving as a bottom electrode; membrane 810 supported on substrate 801 by membrane supports 830; a first set of saw-tooth shaped comb fingers 820 electrically connected to the bottom electrode which is attached to or an integral part of substrate 801; a second set of saw-tooth shaped comb fingers 840 attached to (or being an integral part of) membrane 810; and top electrode 850 attached to membrane 810. The second set of saw-tooth shaped comb fingers 840 are electrically connected to the top electrode 850, and may be considered a part of the top electrode 850. If membrane 810 is conductive, top electrode 850 may be an integral part of membrane 810. If membrane 810 is not conductive, it is then operatively preferable to electrically connect the top electrode 850 with the second set of comb fingers 840 through holes on the membrane 810.

Membrane 810 is separated from substrate 801 to make room for saw-tooth shaped comb fingers 820 and 840. The first set of saw-tooth shaped comb fingers 820 and the second set of saw-tooth shaped comb fingers 840 interdigitate with each other with adjacent comb fingers 820 and 840 facing each other and separated by a narrow space 860. The first set of saw-tooth shaped comb fingers 820 may be substantially stationary with substrate 801, while the second set of saw-tooth shaped comb fingers 840 are movable in the vertical z-direction due to the flexibility of membrane 810. When a voltage is applied to one of the two sets of comb fingers 820 and 840 with respect to the other, asymmetrical distribution of electrical field lines around each comb finger 820 or 840 results in an electrostatic force in the z-direction to move the second set of comb fingers 840 upward in that direction. Because the movable comb fingers 840 are attached to membrane 810 which is anchored through membrane supports 830 to substrate 801, there is a spring force applied to the movable comb fingers 840 generally in the z-direction. In addition, when the comb driver electrostatic transducer 800 is at a level position, the movable comb fingers 840 and membrane 810 (and top electrode 850) together also experience gravity. These forces together determine the motion dynamics (or equilibrium in a stationary condition) of the movable comb fingers 840.

In transmission mode, an electrical input signal is applied as a voltage signal across the first set of comb fingers 820 and the second set of comb fingers 840. The electrical input signal generates a z-direction displacement of the movable comb fingers 840, and further that of membrane 810 (and top electrode 850 if applicable), which interfaces with a medium (not shown). At a proper frequency range, this motion generates ultrasonic waves in the medium. In reception mode, a reverse process takes place. Ultrasonic waves in the medium drive the membrane 810 and the movable comb fingers 840, the motion of which then generates an output electric signal detected by a reception circuit (not shown). Specifically, the z-direction displacement of the movable comb fingers 840 causes a change of the capacitive area (an overlap area) between the two sets of comb fingers 820 and 840 and thus results in a variation of the capacitance formed therebetween. The variation of the capacitance is detected by the reception circuit in a manner similar to that in conventional cMUT.

The comb driver electrostatic transducer 800 is distinct from the conventional parallel plate cMUT, which does not have a comb driver with comb fingers. The cMUT comb driver electrostatic transducer 800 is potentially more linear and has much larger displacement than parallel plate cMUT with the same electrode separation, especially in transmission (TX) operation which involves large displacement. In addition, the maximum z-direction displacement of the comb driver electrostatic transducer 800 can be significantly greater than the minimum electrode gap (e.g., the gap defined by the narrow space 860 between two adjacent comb fingers 820 and 840) in the comb driver.

The comb driver electrostatic transducer 800 is also distinct from the comb driver cMUT 200 which has straight vertical comb fingers 220 and 240 instead of saw-tooth shaped comb fingers 820 and 840. With a given voltage and minimum gap g, the comb driver electrostatic transducer 800 can potentially have a much greater electrostatic actuation force than the comb driver 204, all with a reasonably small sacrifice on linearity.

In addition to applications in the conventional membrane-based cMUT as shown in FIG. 8, the saw-toothed comb driver may be applied in micro-electromechanical transducers have an embedded springs, such as embedded-spring cMUT (ESCMUT) disclosed in the several patent applications referenced to and incorporated herein, thus taking advantage of the benefits of both embedded springs and comb drivers.

Figure 9:
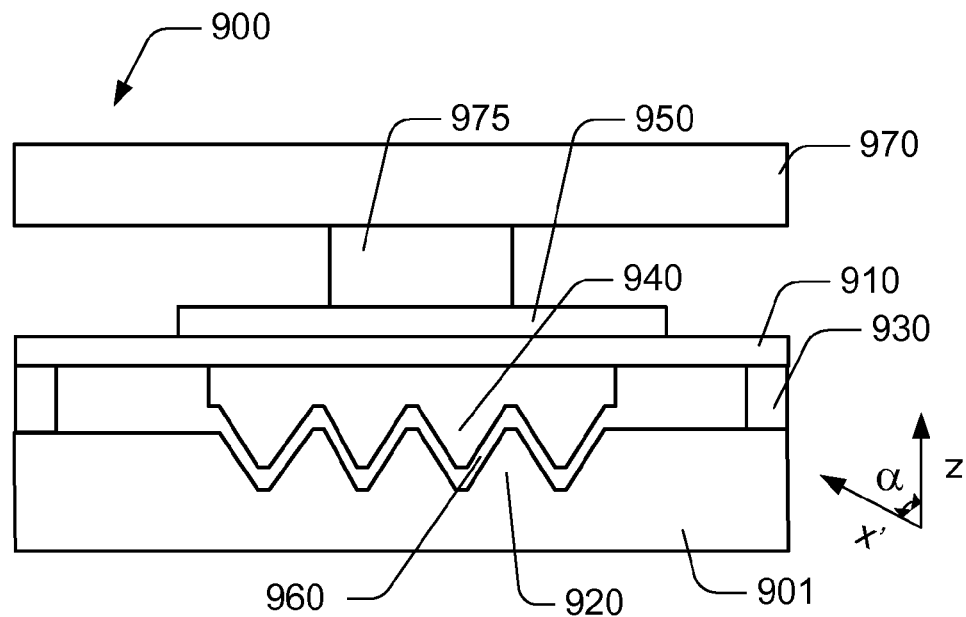
FIG. 9 is a schematic cross-sectional view of an embedded-spring actuator/transducer with a saw-toothed comb driver.

FIG. 9 is a schematic cross-sectional view of an embedded-spring actuator/transducer with a saw-toothed comb driver. The saw-toothed comb driver electrostatic transducer 900 is similar to the comb driver cMUT 300 in FIG. 3 except that the comb driver electrostatic transducer 900 has saw-toothed comb fingers 920 and 940 instead of the straight vertical comb fingers 320 and 340 in the comb driver cMUT 300. The structure of saw-toothed comb driver electrostatic transducer 900 therefore may be understood in a similar way as the comb driver cMUT 300 in FIG. 3. The comb driver electrostatic transducer 900 has the benefit of a saw-toothed comb driver as discussed above.

The comb driver electrostatic transducer 900 includes substrate 901, which may either serve as a bottom electrode or has an attached conductive layer (not shown) as a bottom electrode. A first set of saw-tooth shaped comb fingers 920 are connected to the substrate 901 and electrically connected to the bottom electrode. A spring layer (e.g., a flexible membrane) 910 is connected to the substrate 901 through spring anchors 930. A second set of saw-tooth shaped comb fingers 940 are connected to spring layer 910 and a top electrode 950 placed on the spring layer 910. If the spring layer 910 is made of a conductive material to serve as the top electrode, a separate top electrode 950 may not be needed. The second set of comb fingers 940 are preferably electrically connected to the top electrode 950, and may be considered a part of the top electrode 950.

The first set of saw-tooth shaped comb fingers 920 and the second set of saw-tooth shaped comb fingers 940 interdigitate with each other with adjacent comb fingers 920 and 940 facing each other and separated by a narrow space 960. The first set of comb fingers 920 may be substantially stationary with substrate 901, while the second set of comb fingers 940 are movable in the vertical z-direction due to the flexibility of membrane 910. As illustrated in FIG. 9, when a voltage is applied to one of the two sets of comb fingers 920 and 940 with respect to the other, an asymmetrical distribution of electrical field lines results in an electrostatic force in the z-direction to move the second set of comb fingers 940 upward in that direction. Because the movable comb fingers 940 are attached to spring layer 910 which is anchored through spring anchors 930 to substrate 901, there is a spring force applied to the movable comb fingers 940 generally in the z-direction. The electrostatic force, spring force, and gravity together determine the motion dynamics (or equilibrium in a stationary condition) of the movable comb fingers 940. For micromachined ultrasonic transducers which have very light movable components, the gravity may play an insignificant role.

A surface plate (mass layer) 970 is connected to the top electrode 950, and thus to the spring layer 910, through spring-mass connector 975. The surface plate 970 may be adapted to interface with a medium. The surface plate 970 is actuated by the applied electrode field between two sets of comb fingers 920 and 940 to transmit the ultrasound into the medium. Conversely, ultrasound can be detected if it impinges on the surface plate 970 to cause the capacitance between two sets of comb fingers 920 and 940 to change. The surface plate 970 increases the equivalent mass and spring constant in the transducer, and thus may affect the operating frequency of the transducer.

The comb driver electrostatic transducer 900 may be operated in two different modes. In a receiver mode, ultrasonic waves in a medium is picked up by the surface plate 970 which moves in a piston fashion to exert a force on the spring layer 910 through the spring-mass connector 975. The spring layer 910 is anchored at its two ends at spring anchors 930. When pushed by the surface plate 970 through the spring-mass connectors 975, the spring layer 910, the top electrode 950, and the second set of comb fingers 940 move relative to the bottom electrode and the first set of comb fingers 920, causing a change in the capacitance of the capacitor formed between the two sets of comb fingers 920 and 940. The capacitance change is picked up by the device circuitry as the signal. In a transmitter mode, the movable comb fingers 940 are driven by the electrostatic force of the asymmetrical electrical field created by the device circuitry to cause a motion of the top electrode 950. The motion of the top electrode 950 moves the surface plate 970, which interfaces with the surrounding medium to transmit an ultrasound signal.

The comb driver electrostatic transducer 900 may be only a portion of a single ESCMUT in practice. Despite the similarity between the lower parts of the comb driver electrostatic transducer 900 and the comb driver electrostatic transducer 800, they may have very different overall structure as described in the patent applications referenced and incorporated herein.

Figure 10:
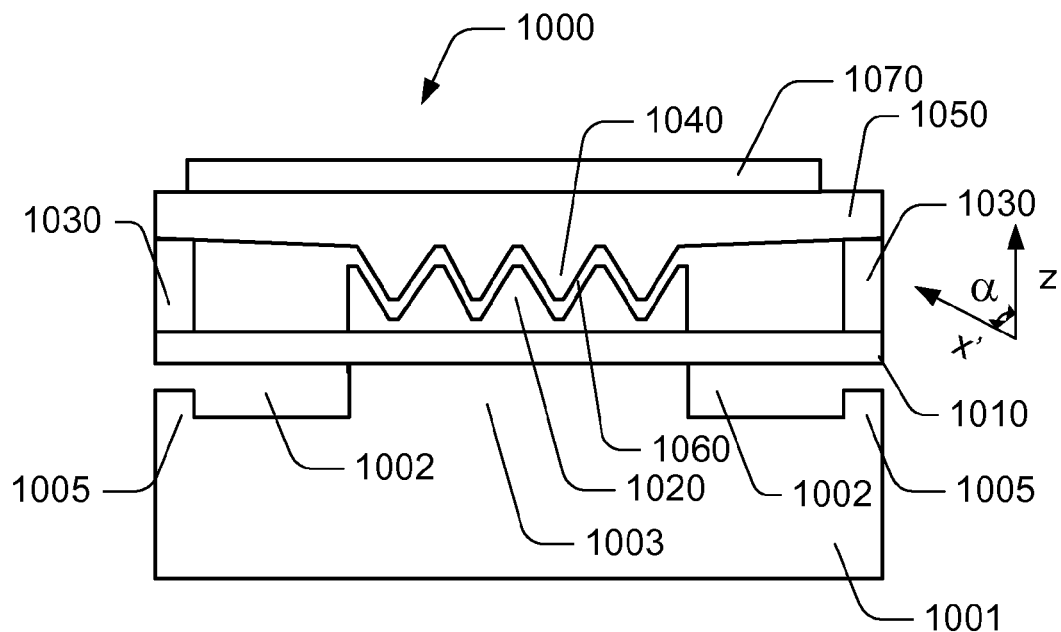
FIG. 10 is a schematic cross-sectional view of another embedded-spring actuator/transducer with a saw-toothed comb driver.

FIG. 10 is a schematic cross-sectional view of another embedded-spring actuator/transducer, such as embedded spring cMUT (ESCMUT), with a saw-toothed comb driver. The saw-toothed comb driver electrostatic transducer 1000 is similar to the comb driver cMUT 400 in FIG. 4 except that the comb driver electrostatic transducer 1000 has saw-toothed comb fingers 1020 and 1040 instead of the straight vertical comb fingers 420 and 440 in the comb driver cMUT 400. The structure of saw-toothed comb driver electrostatic transducer 1000 therefore may be understood in a similar way as the comb driver cMUT 400 in FIG. 4. The comb driver electrostatic transducer 1000 has the benefit of a saw-toothed comb driver as discussed above.

The comb driver electrostatic transducer 1000 has a substrate 1001, on top of which are spring anchor 1003 having two sidewalls on two opposing sides bordering cavities 1002 and motion stoppers 1005. The substrate of 1001 may be made of either a nonconductive material or a conductive material such as silicon or polysilicon.

The comb driver electrostatic transducer 1000 further has these components: a spring layer 1010 which is preferably an elastic membrane; a first set of saw-tooth shaped comb fingers 1020 connected to the spring layer 1010; a surface plate 1050 connected to the spring layer 1010 through spring-plate connectors 1030; a second set of comb fingers 1040 connected to the surface plate 1050; and a top electrode 1070 connected to the surface plate 1050.

The first set of saw-tooth shaped comb fingers 1020 are preferably electrically connected to a bottom electrode which may be served by the spring layer 1010 or the spring anchor 1003 if either of which is made of a conductive material, or served by a separate conductive layer (not shown) connected to the spring layer 1010. If so connected, the first set of comb fingers 1020 may be considered a part of the bottom electrode. The first set of saw-tooth shaped comb fingers 1020 may be made directly on the spring layer 1010. If the spring layer 1010 is conductive, it may facilitate the electrical connection between the comb fingers 1020 and the bottom electrode. The spring layer 1210 may also serve as the bottom electrode or a part thereof.

The second set of saw-tooth shaped comb fingers 1040 are preferably electrically connected to the top electrode 1070, and if so connected, may be considered a part of the top electrode 1070.

The two sets of comb fingers 1020 and 1040 interdigitate with each other to form a comb driver. Adjacent comb fingers 1020 and 1040 face each other to define a narrow space 1060. The first set of comb fingers 1020 may be substantially stationary with substrate 1002, while the second set of comb fingers 1040 are movable in the vertical z-direction due to the flexibility of spring layer 1010 which forms a springy cantilever anchored at spring anchor 1003. Similar to the comb driver electrostatic transducer 800 in FIG. 8 and the comb driver electrostatic transducer 900 in FIG. 9, when a voltage is applied to one of the two sets of comb fingers 1020 and 1040 with respect to the other, an asymmetrical distribution of electrical field lines results in an electrostatic force in the z-direction to move the second set of comb fingers 1040 upward in that direction. Because the movable comb fingers 1040 are attached to spring layer 1010 which is anchored through spring anchors 1003 to substrate 1002, there is a spring force applied to the movable comb fingers 1040 generally in the z-direction. The electrostatic force, spring force, and gravity together determine the motion dynamics (or equilibrium in a stationary condition) of the movable comb fingers 1040.

The comb driver electrostatic transducer 1000 may be only a portion of a complete embedded-spring actuator/transducer element such as an ESCMUT element (not shown). Depending on how and where the comb driver electrostatic transducer 1000 is taken from the complete ESCMUT element, for example, the two cavities 1001 shown in FIG. 10 may either belong to a different and separate cavity, or just two portions of a same circular or extended cavity. Likewise, depending on how and where the comb driver electrostatic transducer 1000 is taken from a complete ESCMUT element, the two spring-plate connectors 1030 may either each be a part of a different and separate connector, or just two portions of the same circular or extended connector.

It is impossible to exhaustively describe all possible situations where a conventional parallel or a straight vertical comb driver may be replaced with the above described saw-toothed actuator/transducer. FIGS. 7-10 are just several exemplary embodiments.

Fabrication Methods

There are many possible fabrication methods to make an electrostatic actuator/transducer such as a cMUT with a comb driver described above. The available processes include wafer bonding technology, bulk silicon micromachining and surface micromachining technology or the combinations of them. Except for forming the comb drivers, other process steps are similar to those of the fabrication processes of fabricating cMUTs and ESCMUTs disclosed in the several patent applications referenced to herein.

In the following, some exemplary fabrication methods are described. Although the exemplary methods of forming the comb driver are illustrated to form the comb driver on a substrate, the same or similar methods may be used for forming the comb driver on a spring membrane layer or a surface plate, during any fabrication method selected for fabricating the electrostatic actuator/transducer (such as cMUT) with a saw-toothed comb driver. It is noted that some steps in the fabrication methods shown in FIGS. 11-14 may be optional (even if the step is not explicitly described as being optional in the following description), and the fabrication methods are not limited to any particular order of the steps performed in the exemplary processes. It is further noted that the processes are illustrated with reference to only a section of an actual wafer on which multiple cMUT elements and devices may be fabricated. The exemplary arrangements of multiple cMUT elements and devices are described in the several patent applications referenced to and incorporated herein.

FIG. 11 shows a process to make a cMUT with a comb driver.

At step 1 (FIG. 11.1), an SOI wafer 1101 is made of a device layer 1111, an oxide layer (box layer) 1112 and a supporting wafer 1113. The device layer 1111 is patterned to a desired shape to form a flexible membrane layer and anchors. For example, thinned portions 1116 may become flexible membrane layer and portions 1115 may become anchors for the comb finger to be formed.

At step 2 (FIG. 11.2), another SOI wafer 1102 is made of a device layer 1121, an oxide layer (box layer) 1122 and a supporting wafer 1123. The device layer 1121 is patterned to a desired pattern in which portions 1125 are to become a bottom electrode and anchors for comb fingers. The trenches 1126 patterned on the device layer 1121 may reach the oxide layer of 1122 to achieve insulation.

At step 3 (FIG. 11.3), a silicon layer 1130 with desired thickness is bonded on the SOI wafer 1101 formed in the FIG. 11.1. The silicon layer 1130 can be made of a device layer in a SOI wafers or a prime wafer which is ground and polished to the desired thickness after bonding.

At step 4 (FIG. 11.4), a desired recession pattern 1135 is formed on the silicon layer 1130.

At step 5 (FIG. 11.5), the silicon layer 1130 is patterned to form two sets of comb fingers 1120 and 1140. The first set of comb fingers 1120 are connected to anchors 1115, while the second set of comb fingers 1140 will be connected to electrode/anchor 1125 of FIG. 11.5 in the next step.

At step 6 (FIG. 11.6), the patterned SOI wafer 1102 in the FIG. 2 is bonded to 1130. The bonding can be done with silicon fusion bonding, eutectic bonding, thermal compression bonding, or any other suitable bonding method.

At step 7 (FIG. 11.7), the supporting wafer 1113 and oxide layer 1112 are removed to form the device layer 1111. Vias may be formed through oxide layer 1122 and supporting wafer 1123 to access the bottom electrode 1125 if needed.

At step 8 (FIG. 11.8), a metal layer 1180 may be deposited and patterned as a top electrode. The silicon layer 1111 between transducer elements or devices may be removed to achieve insulation between them.

FIG. 12 shows a second process to make a cMUT with a comb driver.

At step 1 (FIG. 12.1), a desired recession pattern is formed on a prime wafer 1201. Protruding portions 1205 partially defining the recession pattern may become the anchors for the comb fingers to be formed.

At step 2 (FIG. 12.2), a silicon layer 1211 with desired thickness is bonded on the wafer 1201. This layer can be made of a device layer in a SOI wafers or a prime wafer which is ground and polished to the desired thickness after bonding.

At step 3 (FIG. 12.3), a desired recession pattern 1215 is formed on the silicon layer 1211. This step is optional.

At step 4 (FIG. 12.4), the silicon layer 1211 is pattern to form comb fingers 1240. Gaps 1225 are formed between the comb fingers 1240.

At step 5 (FIG. 12.5), if the gaps 1225 formed by etching at step 4 are too wide, a layer of thin film 1231 may be conformally deposited or grown to narrow the gaps 1225. This step is optional.

At step 6 (FIG. 12.6), a sacrificial material 1241 is coated or deposited on 1211. Planarization may be done if needed. An opening 1245 may be opened in the sacrificial layer 1241 for membrane anchors.

At step 7 (FIG. 12.7), a dielectric material 1251 may be deposited and patterned to be the anchors for the membrane layer (1261 in FIG. 12.9) if the membrane layer is made of conductive material in later step. This step is optional if the membrane material is non-conductive.

At step 8 (FIG. 12.8), openings 1255 are formed in the sacrificial layer 1241 for the membrane layer (1261 in FIG. 12.9) to attach the comb finger 1240.

At step 9 (FIG. 12.9), the membrane material 1261 is deposited. Vias (not shown) are formed in the membrane layer 1261 to access for the sacrificial etching. The sacrificial layer is then removed and cavities 1270 are sealed by sealing the vias.

At step 10 (FIG. 12.10), a metal layer 1281 may be deposited and patterned as top electrode. The membrane layer 1261 between transducer elements or devices may be removed to achieve insulation between them.

FIG. 13 shows a third process to make a cMUT with a comb driver.

At step 1 (FIG. 13.1), a mask layer 1311 is deposited and patterned on a silicon substrate 1301. The substrate 1301 is then etched to a desired depth. The resultant silicon structures 1305 may become a set of the comb fingers, while trenches 1306 may accommodate another set of comb fingers in a later step. If the mask layer 1311 can be used as a sacrificial layer, it may be kept for the next step. Optionally it may be removed after patterning the substrate 1301.

At step 2 (FIG. 13.2), sacrificial material 1321 is introduced. Preferably, only the top or bottom surfaces of patterned substrate 1301, and not sidewalls, are covered by sacrificial material 1321. This may be done by a number of ways, such as depositing or patterning the sacrificial layer 1321; selectively growing or depositing the sacrificial layer 1321; and conformally depositing sacrificial material and coating, then followed by a time controlled etching. One example is to implant oxygen on silicon substrate 1301 after step 1 (FIG. 13.1). Because the directionality of the implantation, there is almost no oxygen implanted on the sidewall, and the high temperature annealing obtains much thicker oxide layer on the top or bottom surface of the substrate.

At step 3 (FIG. 13.3), a thin sacrificial layer 1331 is conformally deposited, coated, or grown on the substrate 1301. The material of this sacrificial layer 1331 may be the same as or different from that of the sacrificial layer 1321.

At step 4 (FIG. 13.4), openings 1335 are opened in the sacrificial layers 1321 and 1331 for forming anchors of the top membrane layer in later step.

At step 5 (FIG. 13.5), a dielectric material 1341 may be deposited and patterned to be the anchors for a membrane layer (1351 in FIG. 13.6) in later step if the membrane layer is made of a conductive material. This step is optional if the membrane layer material is non-conductive.

At step 6 (FIG. 13.6), a membrane material is deposited to form both comb fingers 1307 in trenches 1306 and a membrane layer 1351 over the comb fingers 1307. If needed, the membrane layer 1351 may be polished.

At step 7 (FIG. 13.7), vias (not shown) are then formed in the membrane layer 1351 for the sacrificial etching. The sacrificial layers 1321 and 1331 are then removed and the resultant cavities 1370 are sealed by sealing the vias.

At step 8 (FIG. 13.8), a metal layer 1380 may be deposited and patterned as top electrode. The membrane layer 1351 between transducer elements or devices may be removed to achieve insulation between them.

FIG. 14 shows a fabrication process to make a cMUT with the saw-toothed comb driver.

At step 1 (FIG. 14.1), a mask layer 1411 is deposited and patterned on a silicon substrate 1401. Trenches 1406 with a desired shape pattern are then formed in the silicon substrate 1401 to result in silicon structures 1420 which may become the first set of the saw-tooth shaped comb fingers 1420. The trenches 1406 themselves constitute the spaces between the saw-tooth shaped comb fingers to interdigitatedly receive the other set of the saw-tooth shaped comb fingers in a later step. In the example shown, the first set of comb fingers 1420 are each saw-tooth shaped, and the trenches 1406 each has inverted saw-tooth shape to define the first set of comb fingers 1420. With this configuration, the second set of comb fingers 1440 to be formed in the trenches 1406 are also each saw-tooth shaped to interdigitate with the first set of comb fingers 1420.

If the mask layer 1411 can be used as a sacrificial layer, it may be kept for the next step. Optionally it may be removed after substrate patterning.

The trenches 1406 with proper slope may be made of various methods. For example, they may be formed using anisotropic wet etching (e.g. KOH, and TMAH), anisotropic dry etch and oxidation. They may also be formed with the combination of those methods. For example, narrow trenches 1406a may be formed first as shown in FIG. 14.1.1. One or multiple steps of oxidations and oxide removing may be used to shape the trench walls to a desired shape as shown in FIG. 14.1.2 to form trenches 1406b of a desired shape.

At step 2 (FIG. 14.2), a thin sacrificial layer 1421 is conformally deposited, coated, or grown on the substrate 1401. The material of the sacrificial layer 1421 may be the same as or different from that of the mask layer 1411.

At step 3 (FIG. 14.3), openings 1415 are opened in the remaining mask layer 1411 and the sacrificial layer 1421 for forming the anchors of the top membrane layer 1410 in later step.

At step 4 (FIG. 14.4), a dielectric material 1431 may be deposited and patterned to form the anchors of the membrane layer 1410 if the membrane layer 1410 is made of conductive material. This step is optional if the membrane layer 1410 is made of a non-conductive material.

At step 5 (FIG. 14.5), a membrane material is deposited to form both the saw-tooth shaped comb fingers 1440 in trenches 1406 and the membrane layer 1410 on top of the saw-tooth shaped comb fingers 1440. If needed, the membrane layer 1410 may be polished.

At step 6 (FIG. 14.6), vias (not shown) are formed in the membrane layer 1410 for the sacrificial etching. The sacrificial layer 1421 is removed to form cavities 1460 and cavities 1470. Cavities 1460 become the separation gaps between saw-tooth shaped comb fingers 1420 and 1440. Cavities 1460 and 1470 may be sealed by sealing the vias.

At step 7 (FIG. 14.7), a metal layer 1481 may be deposited and patterned as top electrode. The membrane layer 1410 between transducer elements or devices may be removed to achieve insulation therebetween.

Surface plates (not shown) may be added on the cMUTs made of the methods in FIGS. 11-14 using the methods described in International Patent Application PCT/IB2006/052658 "MICRO-ELECTRO-MECHANICAL TRANSDUCER HAVING A SURFACE PLATE", filed 3 Aug. 2006, to make the comb driver ESCMUTs shown in FIG. 3 and FIG. 9.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A micromachined ultrasonic transducer comprising:
a base portion having a first electrode including a first plurality of comb fingers; and
an upper portion configured to interface with a medium to transmit and/or receive an ultrasonic signal, the upper portion comprising:
a second plurality of comb fingers interdigitatedly engaging with the first plurality of comb fingers;
a membrane layer including a layer of elastic material that overlies and connects to the second plurality of comb fingers, wherein the elastic material of the membrane layer is formed from a first substance that is a different substance from a second substance from which the second plurality of comb fingers are formed; and a layer of conductive material disposed on the membrane layer on a side of the membrane layer opposite to the second plurality of comb fingers to form at least part of a second electrode, wherein the membrane layer is a spring structure movable along a z-direction for relative movement between the second plurality of comb fingers and the first plurality of the comb fingers, the membrane layer is an insulating material, and the layer of conductive material is electrically connected to the second plurality of comb fingers through at least one hole in the membrane layer.

2. The micromachined ultrasonic transducer as recited in claim 1, wherein the membrane layer is disposed above the second plurality of comb fingers and includes at least one comb finger anchor to connect to at least one of the second plurality of comb fingers.

3. The micromachined ultrasonic transducer as recited in claim 1, which is a capacitive micromachined ultrasonic transducer, wherein the first plurality of comb fingers and the second plurality of comb fingers, when interdigitatedly engaging with each other, form a capacitor having a capacitance varying based at least in part on the relative movement between the second plurality of comb fingers and the first plurality of comb fingers.

4. The micromachined ultrasonic transducer as recited in claim 1, wherein
at least one of the first plurality of comb fingers is saw-tooth shaped with a first skewed side at a first skew angle relative to the z-direction, and
at least one of the second plurality of comb fingers is saw-tooth shaped with a second skewed side at a second skew angle relative to the z-direction facing the first skewed side of the at least one of the first plurality of comb fingers.

5. The micromachined ultrasonic transducer as recited in claim 4, wherein:
the first skew angle and the second skew angle are substantially close to each other such that the first skewed side and the second skewed side are substantially parallel to each other; and
the at least one of the first plurality of comb fingers and the at least one of the second plurality of comb fingers conformally engage with each other.

6. The micromachined ultrasonic transducer as recited in claim 1, wherein the elastic material of the membrane layer is a deposited elastic layer of the first substance.

7. An electrostatic device comprising:
a base portion having a first electrode including a first saw-tooth shaped comb finger with a first skewed side at a first skew angle relative to a z-direction; and
an upper portion having a second electrode including a second saw-tooth shaped comb finger with a second skewed side at a second skew angle relative to the z-direction facing the first skewed side of the first saw-tooth shaped comb finger, wherein:
the second electrode is connected to a spring structure and movable along the z-direction for relative movement between the second saw-tooth shaped comb finger and the first saw-tooth shaped comb finger;
the upper portion is adapted to perform at least one of an actuation function or a sensor function; and
the spring structure is a membrane layer of a first material different from a second material used for the second saw-tooth shaped comb finger, the membrane layer extending across the second saw-tooth shaped comb finger.

8. The electrostatic device as recited in claim 7, wherein:
the first electrode includes a first plurality of saw-tooth shaped comb fingers; and the second electrode includes a second plurality of saw-tooth shaped comb fingers interdigitatedly engaging with the first plurality of saw-tooth shaped comb fingers.

9. The electrostatic device as recited in claim 7, wherein the first skew angle and the second skew angle are substantially close to each other such that the first skewed side and the second skewed side are substantially parallel to each other.

10. The electrostatic device as recited in claim 7, wherein the first skew angle and the second skew angle are greater than 10° and smaller than 80°.

11. The electrostatic device as recited in claim 7, wherein the first saw-tooth shaped comb finger and the second saw-tooth shaped comb finger conformally engage with each other.

12. The electrostatic device as recited in claim 7 wherein the membrane layer is conductive and supported by dielectric membrane supports anchored at the base portion.

13. The electrostatic device as recited in claim 7, wherein the second electrode includes an electrode layer disposed on the membrane layer on a side of the membrane layer opposite to the second comb finger, the electrode layer being of a material different from the first material of the membrane layer.

14. The electrostatic device as recited in claim 13, wherein:
the electrode layer a layer of a conductive material different from an insulating material of the membrane layer; and
the electrode layer is electrically connected to the second comb finger through a hole in the membrane layer.

15. The electrostatic device as recited in claim 7, wherein:
the upper portion further includes a surface plate for interfacing with a medium; and
the surface plate is more rigid than the membrane layer, is disposed on top of the second electrode, and is connected to the membrane layer through a spring-plate connector.

16. The electrostatic device as recited in claim 7, wherein:
the first material is a same substance as the second material; and
the first material is different from the second material at least by being formed separately during fabrication of the membrane layer.

17. A micromachined ultrasonic transducer comprising:
a base portion having a first electrode including a first plurality of comb fingers; and
an upper portion having a second electrode, the second electrode including a second plurality of comb fingers interdigitatedly engaging with the first plurality of comb fingers, wherein:
the second electrode is connected to a spring structure and movable along a z-direction to engage and disengage the second plurality of comb fingers and the first plurality of the comb fingers;
the spring structure includes a spring layer disposed below the first plurality of comb fingers and supported by a spring anchor connected to the base portion;
the second plurality of comb fingers are connected to a support plate which is connected to the spring layer through spring-plate connectors; and
the upper portion is adapted to interface with a medium to transmit and/or receive an ultrasonic signal.

18. The micromachined ultrasonic transducer as recited in claim 17, wherein
- at least one of the first plurality of comb fingers is saw-tooth shaped with a first skewed side at a first skew angle relative to the z-direction; and
- at least one of the second plurality of comb fingers is saw-tooth shaped with a second skewed side at a second skew angle relative to the z-direction facing the first skewed side of the at least one of the first plurality of comb fingers.

19. The micromachined ultrasonic transducer as recited in claim 18, wherein:
- the first skew angle and the second skew angle are substantially close to each other such that the first skewed side and the second skewed side are substantially parallel to each other; and
- the at least one of the first plurality of comb fingers and the at least one of the second plurality of comb fingers conformally engage with each other.

* * * * *